(12) United States Patent
Redington

(10) Patent No.: US 10,272,241 B2
(45) Date of Patent: Apr. 30, 2019

(54) METHODS FOR MODULATING AUTOPHAGY USING REMOTE ISCHEMIC CONDITIONING

(71) Applicant: The Hospital for Sick Children, Toronto (CA)

(72) Inventor: Andrew Redington, Cincinnati, OH (US)

(73) Assignee: The Hospital for Sick Children, Toronto (CA)

( * ) Notice: Subject to any disclaimer, the term of this patent is extended or adjusted under 35 U.S.C. 154(b) by 641 days.

(21) Appl. No.: 14/774,835

(22) PCT Filed: Mar. 14, 2014

(86) PCT No.: PCT/IB2014/001426
§ 371 (c)(1),
(2) Date: Sep. 11, 2015

(87) PCT Pub. No.: WO2014/167423
PCT Pub. Date: Oct. 16, 2014

(65) Prior Publication Data
US 2016/0045726 A1    Feb. 18, 2016

Related U.S. Application Data

(60) Provisional application No. 61/798,622, filed on Mar. 15, 2013.

(51) Int. Cl.
*A61N 1/32* (2006.01)
*A61B 17/135* (2006.01)
*A61K 45/06* (2006.01)
*A61B 17/12* (2006.01)
*A61B 17/132* (2006.01)

(52) U.S. Cl.
CPC ............ *A61N 1/32* (2013.01); *A61B 17/1204* (2013.01); *A61B 17/132* (2013.01); *A61B 17/135* (2013.01); *A61K 45/06* (2013.01)

(58) Field of Classification Search
CPC . A61B 17/1204; A61B 17/132; A61B 17/135; A61K 45/06; A61N 1/32
See application file for complete search history.

(56) References Cited

U.S. PATENT DOCUMENTS 3,552,383 A   1/1971   Krueger et al.
4,106,002 A   8/1978   Hogue, Jr.
(Continued)

FOREIGN PATENT DOCUMENTS

AU   2011237461 A1   11/2012
CA      2692463 A1    1/2009
(Continued)

OTHER PUBLICATIONS

International Search Report and Written Opinion for Application No. PCT/IB2014/001426 dated Jan. 15, 2015.
(Continued)

*Primary Examiner* — Amanda K Hulbert
(74) *Attorney, Agent, or Firm* — Wolf, Greenfield & Sacks, P.C.

(57) ABSTRACT

The invention contemplates, inter alia, the use of remote ischemic conditioning in the treatment of cancer, neurodegenerative disorders, and gastrointestinal disorders, among others.

17 Claims, 4 Drawing Sheets

(56) References Cited

U.S. PATENT DOCUMENTS

| | | | |
|---|---|---|---|
| 4,206,764 A | 6/1980 | Williams | |
| 4,294,261 A | 10/1981 | Baker et al. | |
| 4,321,929 A | 3/1982 | Lemelson et al. | |
| 4,664,651 A | 5/1987 | Weinshenker et al. | |
| 4,690,151 A | 9/1987 | Utsunomiya et al. | |
| 5,072,736 A | 12/1991 | Ogawa et al. | |
| 5,135,003 A | 8/1992 | Souma | |
| 5,152,770 A * | 10/1992 | Bengmark | A61B 17/12 128/DIG. 25 |
| 5,267,565 A | 12/1993 | Beard | |
| 5,569,304 A | 10/1996 | Ulrich | |
| 5,571,075 A | 11/1996 | Bullard | |
| 5,634,467 A | 6/1997 | Nevo | |
| 5,651,369 A | 7/1997 | Tomita | |
| 5,687,732 A | 11/1997 | Inagaki et al. | |
| 6,020,334 A | 2/2000 | Fukushi et al. | |
| 6,152,881 A | 11/2000 | Raines et al. | |
| 6,210,423 B1 | 4/2001 | Kim | |
| 6,251,080 B1 | 6/2001 | Henkin et al. | |
| 6,303,649 B1 | 10/2001 | Hattori et al. | |
| 6,344,025 B1 | 2/2002 | Inagaki et al. | |
| 6,485,429 B2 | 11/2002 | Forstner | |
| 6,550,482 B1 | 4/2003 | Burbank et al. | |
| 6,626,840 B2 | 9/2003 | Drzewiecki et al. | |
| 6,650,943 B1 | 11/2003 | Whitechurst et al. | |
| 6,660,759 B1 | 12/2003 | Hattori et al. | |
| 6,670,362 B2 | 12/2003 | Banks et al. | |
| 6,702,720 B2 | 3/2004 | Dardik | |
| 6,719,704 B2 | 4/2004 | Narimatsu et al. | |
| 6,858,012 B2 | 2/2005 | Burns et al. | |
| 6,962,599 B2 | 11/2005 | Hui | |
| 7,004,907 B2 | 2/2006 | Banet et al. | |
| 7,018,335 B2 | 3/2006 | Kario et al. | |
| 7,048,702 B2 | 5/2006 | Hui | |
| 7,314,478 B2 | 1/2008 | Hui | |
| 7,338,410 B2 | 3/2008 | Dardik | |
| 7,374,540 B2 | 5/2008 | Schnall | |
| 7,390,303 B2 | 6/2008 | Dafni | |
| 7,517,312 B2 | 4/2009 | Loeb et al. | |
| 7,615,548 B2 | 11/2009 | Gottlieb et al. | |
| 7,635,722 B1 | 12/2009 | Bachynsky et al. | |
| 7,689,286 B2 | 3/2010 | Pastore et al. | |
| 7,717,855 B2 | 5/2010 | Caldarone et al. | |
| 8,114,026 B2 | 2/2012 | Leschinsky | |
| 8,246,548 B2 | 8/2012 | Naghavi et al. | |
| 8,753,283 B2 | 6/2014 | Leschinsky | |
| D708,338 S | 7/2014 | Ganske et al. | |
| D709,048 S | 7/2014 | Ganske et al. | |
| D709,197 S | 7/2014 | Ganske et al. | |
| 8,764,789 B2 | 7/2014 | Ganske et al. | |
| 8,790,266 B2 | 7/2014 | Caldarone et al. | |
| 8,911,469 B2 | 12/2014 | Raheman | |
| 9,119,759 B2 | 9/2015 | Caldarone et al. | |
| 9,119,761 B2 | 9/2015 | Caldarone et al. | |
| 9,205,019 B2 | 12/2015 | Ganske et al. | |
| 9,393,025 B2 | 7/2016 | Caldarone | |
| 10,098,779 B2 | 10/2018 | Caldarone | |
| 2001/0029389 A1 | 10/2001 | Kim | |
| 2002/0143369 A1 * | 10/2002 | Hill | A61N 1/36114 607/9 |
| 2002/0155924 A1 | 10/2002 | Dardik | |
| 2003/0013974 A1 | 1/2003 | Natarajan et al. | |
| 2003/0065270 A1 | 4/2003 | Raines et al. | |
| 2003/0143662 A1 | 7/2003 | Cummings et al. | |
| 2003/0176795 A1 | 9/2003 | Harris et al. | |
| 2003/0216651 A1 | 11/2003 | Burns et al. | |
| 2003/0233118 A1 | 12/2003 | Hui | |
| 2004/0044290 A1 | 3/2004 | Ward et al. | |
| 2004/0064076 A1 | 4/2004 | Bilgi | |
| 2004/0102818 A1 | 5/2004 | Hakky et al. | |
| 2004/0134492 A1 | 7/2004 | Dardik | |
| 2004/0241634 A1 | 12/2004 | Millis et al. | |
| 2004/0255956 A1 | 12/2004 | Vinten-Johansen et al. | |
| 2005/0004476 A1 | 1/2005 | Payvar et al. | |
| 2005/0027218 A1 | 2/2005 | Filtvedt et al. | |
| 2005/0070405 A1 | 3/2005 | Egger | |
| 2005/0159640 A1 | 7/2005 | Barbut et al. | |
| 2005/0177078 A1 | 8/2005 | Loeb et al. | |
| 2006/0024779 A1 | 2/2006 | Cummings et al. | |
| 2006/0052712 A1 | 3/2006 | Poliac et al. | |
| 2006/0052713 A1 | 3/2006 | Poliac et al. | |
| 2006/0052714 A1 | 3/2006 | Poliac et al. | |
| 2006/0058717 A1 | 3/2006 | Hui et al. | |
| 2006/0100639 A1 | 5/2006 | Levin et al. | |
| 2006/0142663 A1 | 6/2006 | Sawanoi et al. | |
| 2006/0167390 A1 | 7/2006 | Hui | |
| 2007/0005106 A1 | 1/2007 | Adducci | |
| 2007/0150005 A1 | 6/2007 | Sih et al. | |
| 2008/0081963 A1 | 4/2008 | Naghavi et al. | |
| 2008/0097385 A1 | 4/2008 | Vinten-Johansen et al. | |
| 2008/0139949 A1 | 6/2008 | Caldarone et al. | |
| 2008/0222769 A1 | 9/2008 | Natonson et al. | |
| 2009/0137884 A1 | 5/2009 | Naghavi et al. | |
| 2009/0192128 A1 | 7/2009 | Worcel et al. | |
| 2009/0221649 A1 | 9/2009 | Krahn et al. | |
| 2009/0238852 A1 | 9/2009 | Kennedy et al. | |
| 2009/0287069 A1 | 11/2009 | Naghavi et al. | |
| 2009/0324748 A1 | 12/2009 | Dobson | |
| 2010/0081941 A1 | 4/2010 | Naghavi et al. | |
| 2010/0105993 A1 | 4/2010 | Naghavi et al. | |
| 2010/0160444 A1 | 6/2010 | Gottlieb et al. | |
| 2010/0160799 A1 | 6/2010 | Caldarone et al. | |
| 2010/0185220 A1 | 7/2010 | Naghavi et al. | |
| 2010/0292619 A1 | 11/2010 | Redington et al. | |
| 2010/0305607 A1 | 12/2010 | Caldarone et al. | |
| 2010/0322467 A1 | 12/2010 | Reed et al. | |
| 2010/0324429 A1 | 12/2010 | Leschinsky | |
| 2010/0328142 A1 | 12/2010 | Zoughi et al. | |
| 2011/0152650 A1 | 6/2011 | Donehoo et al. | |
| 2011/0190807 A1 | 8/2011 | Redington et al. | |
| 2011/0238107 A1 * | 9/2011 | Raheman | A61B 5/412 606/202 |
| 2011/0240043 A1 | 10/2011 | Redington | |
| 2011/0251635 A1 | 10/2011 | Caldarone | |
| 2012/0130419 A1 | 5/2012 | Leschinsky | |
| 2012/0265240 A1 | 10/2012 | Ganske et al. | |
| 2012/0277789 A1 | 11/2012 | Caldarone et al. | |
| 2013/0184745 A1 | 7/2013 | Leschinsky | |
| 2013/0211269 A1 | 8/2013 | Leschinsky | |
| 2013/0218196 A1 | 8/2013 | Cheung | |
| 2013/0317581 A1 | 11/2013 | Redington | |
| 2014/0024986 A1 | 1/2014 | Souma | |
| 2014/0296756 A1 | 10/2014 | Ganske et al. | |
| 2014/0349927 A1 | 11/2014 | Weinstock-Rosin et al. | |
| 2016/0015553 A1 | 1/2016 | Caldarone | |
| 2016/0022269 A1 | 1/2016 | Ganske et al. | |
| 2016/0038147 A1 | 2/2016 | Redington | |
| 2016/0038737 A1 | 2/2016 | Redington | |
| 2016/0045726 A1 | 2/2016 | Redington | |
| 2017/0042553 A1 | 2/2017 | Caldarone et al. | |
| 2017/0273695 A1 | 9/2017 | Ganske et al. | |
| 2018/0200140 A1 | 7/2018 | Ganske et al. | |

FOREIGN PATENT DOCUMENTS

| | | |
|---|---|---|
| CN | 2395559 Y | 9/2000 |
| CN | 201098315 Y | 8/2008 |
| CN | 200820123637 | 11/2008 |
| CN | 101317805 A | 12/2008 |
| CN | 201316381 Y | 9/2009 |
| EP | 0 960 598 A1 | 12/1999 |
| EP | 1 016 379 A1 | 7/2000 |
| EP | 1 249 218 A2 | 10/2002 |
| GB | 1323365 A | 7/1973 |
| GB | 2434536 A | 8/2007 |
| JP | 07051276 A | 2/1995 |
| JP | 2001221 A | 1/2001 |
| JP | 2001505472 A | 4/2001 |
| JP | 2002539879 A | 11/2002 |
| RU | 2 253 429 C1 | 6/2005 |
| WO | WO 83/00995 A1 | 3/1983 |
| WO | WO 91/18571 A1 | 12/1991 |
| WO | WO 98/30144 A1 | 7/1998 |
| WO | WO 00/56261 A1 | 9/2000 |

(56) References Cited

FOREIGN PATENT DOCUMENTS

| WO | WO 00/57776 A1 | 10/2000 |
|---|---|---|
| WO | WO 2004/004702 A2 | 1/2004 |
| WO | WO 2005/011503 A1 | 2/2005 |
| WO | WO 2005/077265 A1 | 8/2005 |
| WO | WO 2006/007851 A2 | 1/2006 |
| WO | WO 2006/024871 A1 | 3/2006 |
| WO | WO 2006/030441 A2 | 3/2006 |
| WO | WO 2006/061825 A2 | 6/2006 |
| WO | WO 2006/069170 A2 | 6/2006 |
| WO | WO 2006/099958 A1 | 9/2006 |
| WO | WO 2007/085828 A1 | 8/2007 |
| WO | WO 2008/070164 A2 | 6/2008 |
| WO | WO 2008/148045 A1 | 12/2008 |
| WO | WO 2008/148062 A1 | 12/2008 |
| WO | WO 2009/010810 A2 | 1/2009 |
| WO | WO 2010/132115 A1 | 11/2010 |
| WO | WO 2011/005538 A2 | 1/2011 |
| WO | WO 2011/121402 A2 | 10/2011 |
| WO | WO 2011/127341 A2 | 10/2011 |
| WO | WO 2012/016280 A1 | 2/2012 |
| WO | WO 2012/090068 A2 | 7/2012 |
| WO | WO 2012/142360 A2 | 10/2012 |

OTHER PUBLICATIONS

International Preliminary Report on Patentability for Application No. PCT/IB2014/001426 dated Sep. 24, 2015.
Addison et al., Noninvasive remote ischemic preconditioning for global protection of skeletal muscle against infarction. Am J Physiol Heart Circ Physiol. 2003;285:H1435-1443.
Ali et al., Induced remote ischemic pre-conditioning on ischemia-reperfusion injury in patients undergoing coronary artery bypass. J Coll Physicians Surg Pak. Jul. 2010;20(7):427-431.
Ali et al., Remote ischemic preconditioning reduces myocardial and renal injury after elective abdominal aortic aneurysm repair: a randomized controlled trial. Circulation. Sep. 11, 2007;116(11 Suppl):I98-105.
Andreka et al., Remote ischaemic postconditioning protects the heart during acute myocardial infarction in pigs. Heart. Jun. 2007;93(6):749-52. Epub Apr. 20, 2007.
Babak et al., Ischemic Preconditioning as a Possible Factor for Prevention of Restenosis After Coronary Intervention. Sverdlovsk Regional Center of M.V. Savichevsky. Ekaterinburg, Russian Federation. Cardiovascular diseases: scientific conferenceabstracts of the IXth Russian national congress of cardiovascular surgeons. Moscow. Nov. 2003: Bulletin of the Bakoulev Center for Cardiovascular Surgery of the RAMS—2003.—vol. 4, No. 11: 18-21. Russian.
Bartekova et al., Liver ischemia induced remote preconditioning: role of cardioprotective proteins. 25. ISHR-ES meeting. Jun. 21-25, 2005. Tromsoe, Norway.J Mol Cell Cardiol. 2005;38(6):1004.
Bauer et al., Does preconditioning protect the coronary vasculature from subsequent ischemia/reperfusion injury? Circulation. Aug. 1993;88(2):659-72.
Bell, Remote ischaemic conditioning and ischaemic heart disease. Br J Hosp Med (Lond). Jan. 2014;75(1):C13-6.
Birnbaum et al., Ischemic preconditioning at a distance:reduction of myocardial infarct size by partial reduction of blood supply combined with rapid stimulation of the gastrocnemius muscle in the rabbit. Circulation. Sep. 2, 1997;96(5):1641-6.
Bøtker et al., Prehospital remote ischemic preconditioning reduces infarct size in patients with evolving myocardial infarction undergoing primary percutaneous intervention. Fondation Leducq Transatlantic Network Presentation. Mar. 2009. 23 pgs.
Botker et al., Remote ischaemic conditioning before hospital admission, as a complement to angioplasty, and effect on myocardial salvage in patients with acute myocardial infarction: a randomised trial. Lancet. Feb. 27, 2010;375(9716):727-34.
Botker et al., Upper-limb ischemia during ambulance transfer reduces myocardial perfusion injury in STEMI. Heartwire. Mar. 28, 2009. Featured at i2 Session of AAC. Mar. 28-31, 2009. Last Accessed on Mar. 5, 2012 fromhttp://www.theheart.org/article/951627.do.
Breivik et al., Remote postconditioning by humoral factors in effluent from ischemic preconditioned rat hearts is mediated via PI3K/Akt-dependent cell-survival signaling at reperfusion. Basic Res Cardiol. Jan. 2011;106(1):135-45. doi: 10.1007/s00395-010-0133-0. Epub Nov. 20, 2010.
Brzozowski et al., Ischemic preconditioning of remote organs attenuates gastric ischemia-reperfusion injury through involvement of prostaglandins and sensory nerves. Eur J Pharmacol. Sep. 19, 2004;499(1-2):201-13.
Calbet et al., Effects of ATP-induced leg vasodilation on VO2 peak and leg O2 extraction during maximal exercise in humans. Am J Physiol Regul Integr Comp Physiol. Aug. 2006;291(2):R447-53. Epub Feb. 16, 2006.
Champion et al., A profile of combat injury. J Trauma. May 2003 ;54(5 Suppl):S13-9.
Cheung et al., Randomized controlled trial of the effects of remote ischemic preconditioning on children undergoing cardiac surgery: first clinical application in humans. J Am Coll Cardiol. Jun. 6, 2006;47(11):2277-82.
Choi et al., Effect of remote ischemic preconditioning on renal dysfunction after complex valvular heart surgery: A randomized controlled trial. J Thorac Cardiovasc Surg. 2011;142:148-154.
Crimi et al., Remote ischemic post-conditioning of the lower limb during primary percutaneous coronary intervention safely reduces enzymatic infarct size in anterior myocardial infarction: a randomized controlled trial. JACC Cardiovasc Interv. Oct. 2013;6(10):1055-63.
D'Ascenzo et al., Cardiac remote ischaemic preconditioning reduces periprocedural myocardial infarction for patients undergoing percutaneous coronary interventions: a meta-analysis of randomised clinical trials. EuroIntervention. Apr. 2014;9(12):1463-71. doi: 10.4244/EIJV9I12A244.
D'Ascenzo et al., Remote ischaemic preconditioning in coronary artery bypass surgery: a meta-analysis. Heart. Sep. 2012;98(17):1267-71.
Dave et al., Remote organ ischemic preconditioning protect brain from ischemic damage following asphyxial cardiac arrest. Neurosci Lett. Aug. 14, 2006;404(1-2):170-5. Epub Jun. 15, 2006.
Davies et al., Remote ischemic preconditioning improves outcome at 6 years after elective percutaneous coronary intervention: the CRISP stent trial long-term follow-up. Circ Cardiovasc Interv. Jun. 2013;6(3):246-51. Epub May 21, 2013.
Dickson et al., Rabbit heart can be "preconditioned" via transfer of coronary effluent. Am J Physiol. Dec. 1999;277(6 Pt 2):H2451-7.
Dong et al., Limb ischemic preconditioning reduces infarct size following myocardial ischemia-reperfusion in rats] Sheng Li Xue Bao. Feb. 25, 2004;56(1):41-6. Chinese, Y-Abstract.
Ghaemian et al., Remote ischemic preconditioning in percutaneous coronary revascularization: a double-blind randomized controlled clinical trial. Asian Cardiovasc Thorac Ann. Oct. 2012;20(5):548-54.
Gho et al., Myocardial protection by brief ischemia in noncardiac tissue. Circulation. Nov. 1, 1996;94(9):2193-200.
Gonzalez-Alonso et al., Haemodynamic responses to exercise, ATP infusion and thigh compression in humans: insight into the role of muscle mechanisms on cardiovascular function. J Physiol. May 1, 2008;586(9):2405-17. doi: 10.1113/jphysiol.2008.152058. Epub Mar. 13, 2008.
Gritsopoulos et al., Remote postconditioning is more potent than classic postconditioning in reducing the infarct size in anesthetized rabbits. Cardiovasc Drugs Ther. Jun. 2009;23(3):193-8. Abstract.
Gurusamy et al., Ischaemic preconditioning for liver transplantation. Cochrane Database Syst Rev. 2008:CD006315.
Hahn et al., Remote ischemic pre-conditioning: A novel therapy for acute stroke? Stroke. Aug. 2011;42:2960-2962.
Harkin et al., Ischemic preconditioning before lower limb ischemia—reperfusion protects against acute lung injury. J Vasc Surg. Jun. 2002;35(6):1264-73.

(56) References Cited

OTHER PUBLICATIONS

Hausenloy et al., Effect of remote ischaemic preconditioning on myocardial injury in patients undergoing coronary artery bypass graft surgery: a randomised controlled trial. Lancet. Aug. 18, 2007;370(9587):575-9.
Hausenloy et al., Preconditioning and postconditioning: underlying mechanisms and clinical application. Atherosclerosis. Jun. 2009;204(2):334-41. Epub Nov. 5, 2008.
Hausenloy et al., Remote ischaemic preconditioning: underlying mechanisms and clinical application. Cardiovasc Res. Aug. 1, 2008;79(3):377-86. doi: 10.1093/cvr/cvn114. Epub May 2, 2008.
Hausenloy et al., The therapeutic potential of ischemic conditioning: an update. Nat Rev Cardiol. Jun. 21, 2011;8(11):619-29.
Hoda et al., Remote ischemic perconditioning is effective alone and in combination with intravenous tissue-type plasminogen activator in murine model of embolic stroke. Stroke. Oct. 2012;43(10):2794-9. Epub Aug. 21, 2012.
Holcomb et al., Understanding combat casualty care statistics. J Trauma. Feb. 2006;60(2):397-401.
Hong et al., The effect of remote ischaemic preconditioning on myocardial injury in patients undergoing off-pump coronary artery bypass graft surgery. Anaesth Intensive Care. Sep. 2010;38(5):924-9.
Hoole et al., Cardiac Remote Ischemic Preconditioning in Coronary Stenting (CRISP Stent) Study: a prospective, randomized control trial. Circulation. Feb. 17, 2009;119(6):820-7. Epub Feb. 2, 2009.
Hopper et al., Role and mechanism of PKC in ischemic preconditioning of pig skeletal muscle against infarction. Am J Physiol Regul Integr Comp Physiol. Aug. 2000;279(2):R666-76.
Hu et al., Limb remote ischemic post—conditioning reduces injury and improves long-term behavioral recovery in rats following subarachnoid hemorrhage: Possible involvement of the autophagic process. Molecular Medicine Reports. 2017. 10 pages.
Iliodromitis et al., Increased C reactive protein and cardiac enzyme levels after coronary stent implantation. Is there protection by remote ischaemic preconditioning? Heart. Dec. 2006;92(12):1821-6. Epub Jul. 19, 2006.
Iliodromitis et al., Intravenous atenolol and esmolol maintain the protective effect of ischemic preconditioning in vivo. Eur J Pharmacol. Sep. 19, 2004;499(1-2):163-9.
Jan et al., Limb ischemic preconditioning mitigates lung injury induced by haemorrhagic shock/resuscitation in rats. Resuscitation. Jun. 2011;82(6):760-6. Epub Mar. 12, 2011.
Jenkins et al., Ischaemic preconditioning reduces troponin T release in patients undergoing coronary artery bypass surgery. Heart. Apr. 1997;77(4):314-8.
Jennings, "A Critical Appraisal of the Revised Trauma Score," Australasian Journal of Paramedicine, vol. 2, Issue 1, (2004).
Jensen et al., Remote ischemic preconditioning protects the brain against injury after hypothermic circulatory arrest. Circulation. Feb. 22, 2011;123(7):714-721. Epub Feb. 7, 2011.
Jing et al., Why is autophagy important in human diseases? Exp Mol Med. Feb. 29, 2012;44(2):69-72. doi: 10.3858/emm.2012.44.2.028.
Kanoria et al., Remote ischaemic preconditioning of the hind limb reduces experimental liver warm ischaemia-reperfusion injury. Br J Surg. Jun. 2006;93(6):762-8.
Karuppasamy et al., Remote intermittent ischemia before coronary artery bypass graft surgery: a strategy to reduce injury and inflammation? Basic Res Cardiol. Jun. 2011;106(4):511-9. Epub May 5, 2011.
Kerendi et al., Remote postconditioning. Brief renal ischemia and reperfusion applied before coronary artery reperfusion reduces myocardial infarct size via endogenous activation of adenosine receptors. Basic Res Cardiol. Sep. 2005;100(5):404-12. Epub Jun. 17, 2005.
Kharbanda et al., Ischemic preconditioning prevents endothelial injury and systemic neutrophil activation during ischemia-reperfusion in humans in vivo. Circulation. Mar. 27, 2001;103(12):1624-30.
Kharbanda et al., Remote ischaemic preconditioning protects against cardiopulmonary bypass-induced tissue injury: a preclinical study. Heart. Oct. 2006;92(10):1506-11. Epub Jul. 3, 2006.
Kharbanda et al., Transient limb ischemia induces remote ischemic preconditioning in vivo. Circulation. Dec. 3, 2002;106(23):2881-3.
Kharbanda et al., Translation of remote ischaemic preconditioning into clinical practice. Lancet. Oct. 31, 2009;374(9700):1557-65.
Kin et al., Postconditioning attenuates myocardial ischemia-reperfusion injury by inhibiting events in the early minutes of reperfusion. Cardiovasc Res. Apr. 1, 2004;62(1):74-85.
Koch et al.,. Remote ischemic limb preconditioning after subarachnoid hemorrhage: a phase Ib study of safety and feasibility. Stroke. May 2011;42(5):1387-91. Epub Mar. 17, 2011.
Kolh Remote ischaemic pre-conditioning in cardiac surgery: benefit or not? Eur Heart J. Jan. 2014;35(3):141-3. doi: 10.1093/eurheartj/eht517. Epub Jan. 6, 2014.
Konstantinov et al., Remote ischemic preconditioning of the recipient reduces myocardial ischemia-reperfusion injury of the denervated donor heart via a Katp channel-dependent mechanism. Transplantation. Jun. 27, 2005;79(12):1691-5.
Konstantinov et al., The remote ischemic preconditioning stimulus modifies inflammatory gene expression in humans. Physiol Genomics. Sep. 16, 2004;19(1):143-50. Epub Aug. 10, 2004.
Konstantinov et al., The remote ischemic preconditioning stimulus modifies gene expression in mouse myocardium. J Thorac Cardiovasc Surg. Nov. 2005;130(5):1326-32.
Kottenberg et al., Protection by remote ischemic preconditioning during coronary artery bypass graft surgery with isoflurane but not propofol—a clinical trial. Acta Anaesthesiol Scand. Jan. 2012;56(1):30-8.
Kragh et al., "Practical Use of Emergency Tourniquets to Stop Bleeding in Major Limb Trauma," J Trauma 2008;64: S38-S50.
Lang et al., Myocardial preconditioning and remote renal preconditioning—identifying a protective factor using proteomic methods? Basic Res Cardiol. Mar. 2006;101(2):149-58. Epub Nov. 11, 2005.
Laskey et al., Frequency and clinical significance of ischemic preconditioning during percutaneous coronary intervention. J Am Coll Cardiol. Sep. 17, 2003;42(6):998-1003.
Lazaris et al., Protective effect of remote ischemic preconditioning in renal ischemia/reperfusion injury, in a model of thoracoabdominal aorta approach. J. Surg Res. 2009;154:267-273.
Leconte et al., Delayed hypoxic postconditioning protects against cerebral ischemia in the mouse. Stroke. Oct. 2009;40(10):3349-55. doi: 10.1161/STROKEAHA.109.557314. Epub Jul. 23, 2009.
Leesar et al., Nonelectrocardiographic evidence that both ischemic preconditioning and adenosine preconditioning exist in humans. J Am Coll Cardiol. Aug. 6, 2003;42(3):437-45.
Leesar et al., Preconditioning of human myocardium with adenosine during coronary angioplasty. Circulation. Jun. 3, 1997;95(11):2500-7.
Levy et al., Impotence and Its Medical and Psychosocial Correlates: Results of the Massachusetts Male Aging Study. J Urol. Jan. 1994;151(1):278-80.
Li et al., Late phase of myocardial ischemic preconditioning. Adv Cardiovasc Dis. Oct. 31, 2005;26(5):526-29. Chinese.
Liu et al., Remote ischemic postconditioning promotes the survival of retinal ganglion cells after optic nerve injury. J Mol Neurosci. Nov. 2013;51(3):639-46. doi: 10.1007/s12031-013-0036-2. Epub Jun. 5, 2013.
Loukogeorgakis et al., Remote ischemic preconditioning provides early and late protection against endothelial ischemia-reperfusion injury in humans: role of the autonomic nervous system. J Am Coll Cardiol. Aug. 2, 2005;46(3):450-6.
Loukogeorgakis et al., Transient limb ischemia induces remote preconditioning and remote postconditioning in humans by a K(ATP)-channel dependent mechanism. Circulation. Sep. 18, 2007;116(12):1386-95. Epub Aug. 27, 2007.
Ludman et al., Cardiac preconditioning for ischaemia: lost in translation. Dis Model Mech. Jan.-Feb. 2010;3(1-2):35-8. doi: 10.1242/dmm.003855.

(56) References Cited

OTHER PUBLICATIONS

McCully et al., Adenosine-enhanced ischemic preconditioning: adenosine receptor involvement during ischemia and reperfusion. Am J Physiol Heart Circ Physiol. Feb. 2001;280(2):H591-602.

Meng et al., Upper limb ischemic preconditioning prevents recurrent stroke in intracranial arterial stenosis. Neurology. Oct. 30, 2012;79(18):1853-1861. Epub Oct. 3, 2012.

Michel et al., Double blind randomized controlled crossover studies of the effects of remote preconditioning on the exercise performance of elite swimmers. Presented at the 21st Annual National Pediatric Resident and Fellow Research Competition. May 14, 2009.

Michel et al., Remote preconditioning improves maximal performance in highly trained athletes. Med Sci Sports Exerc. Jul. 2011;43(7):1280-6.

Miki et al., Captopril potentiates the myocardial infarct size-limiting effect of ischemic preconditioning through bradykinin B2 receptor activation. J Am Coll Cardiol. Nov. 15, 1996;28(6):1616-22.

Moretti et al., The EUROpean and Chinese cardiac and renal Remote Ischemic Preconditioning Study (EURO-CRIPS): study design and methods. J Cardiovasc Med (Hagerstown). May 22, 2014. [Epub ahead of print].

Mortensen et al., Limitations to systemic and locomotor limb muscle oxygen delivery and uptake during maximal exercise in humans. J Physiol. Jul. 1, 2005;566(Pt 1):273-85. Epub Apr. 28, 2005.

Mortensen et al., Restrictions in systemic and locomotor skeletal muscle perfusion, oxygen supply and VO2 during high-intensity whole-body exercise in humans. J Physiol. May 15, 2008;586(10):2621-35. doi: 10.1113/jphysiol.2007.149401. Epub Mar. 27, 2008.

Mossop, The next sports performance-enhancement fad? Blood pressure cuffs. Playbook: The Wired World of Sports. Dec. 17, 2010. Accessed from http://www.wired.com/playbook/2010/12/ischemic-preconditioning/. 4 pages.

Munk et al., High-intensity interval training may reduce in-stent restenosis following percutaneous coronary intervention with stent implantation a randomized controlled trial evaluating the relationship to endothelial function and inflammation. Am Heart J. Nov. 2009;158(5):734-741.

Munk et al., Remote ischemic conditioning in patients with myocardial infarction treated with primary angioplasty: impact on left ventricular function assessed by comprehensive echocardiography and gated single-photon emission CT. Circ Cardiovasc Imaging. Nov. 2010;3(6):656-62. Epub Sep. 8, 2010.

Murry et al., Preconditioning with ischemia: a delay of lethal cell injury in ischemic myocardium. Circulation. Nov. 1986;74(5):1124-36.

Nandagopal et al., Critical role for nitric oxide signaling in cardiac and neuronal ischemic preconditioning and tolerance. J Pharmacol Exp Ther. May 2001;297(2):474-8.

Noda et al., Evidence for the delayed effect in human ischemic preconditioning. J Amer College Cardiol. 1999;34.7:1966-74.

Olive et al., Blood flow and muscle fatigue in SCI individuals during electrical stimulation. J Appl Physiol (1985). Feb. 2003;94(2):701-8. Epub Oct. 11, 2002.

Olive et al., Increasing blood flow before exercise in spinal cord-injured individuals does not alter muscle fatigue. J Appl Physiol (1985). Feb. 2004;96(2):477-82. Epub Sep. 23, 2003.

O'Riordan, Remote ischemic conditioning increases myocardial salvage during acute MI. Heartwire. Feb. 26, 2010; http://www.theheart.org/article/1050605.do, 1 page.

Oxenham et al., Angiotensin-converting enzyme inhibitor treatment after myocardial infarction. A selective approach for maximum benefit. J Am Coll Cardiol. Dec. 2000;36(7):2054-5.

Pang et al., Acute ischaemic preconditioning protects against skeletal muscle infarction in the pig. Cardiovasc Res. Jun. 1995;29(6):782-8.

Pang et al., Effector mechanism of adenosine in acute ischemic preconditioning of skeletal muscle against infarction. Am J Physiol. Sep. 1997;273(3 Pt 2):R887-95.

Pasupathy et al., Ischaemic preconditioning protects against ischaemia/reperfusion injury: emerging concepts. Eur J Vasc Endovasc Surg. Feb. 2005;29(2):106-15.

Peng et al., The protective effects of ischemic and calcitonin gene-related peptide-induced preconditioning on myocardial injury by endothelin-1 in the isolated perfused rat heart. Life Sci. 1996;59(18):1507-14.

Penttila et al., Ischemic preconditioning does not improve myocardial preservation during off-pump multivessel coronary operation. Ann Thorac Surg. Apr. 2003;75(4):1246-52; discussion 1252-3.

Peralta et al., Liver ischemic preconditioning: a new strategy for the prevention of ischemia-reperfusion injury. Transplant Proc. Aug. 2003;35(5):1800-2.

Prunier et al., The RIPOST-MI study, assessing remote ischemic perconditioning alone or in combination with local ischemic postconditioning in ST-segment elevation myocardial infarction. Basic Res Cardiol. Mar. 2014;109(2):400. doi: 10.1007/s00395-013-0400-y. Epub Jan. 10, 2014.

Przyklenk et al., Regional ischemic 'preconditioning' protects remote virgin myocardium from subsequent sustained coronary occlusion. Circulation. Mar. 1993;87(3):893-9.

Qi et al., AKT/GSK3β-dependent autophagy contributes to the neuroprotection of limb remote ischemic postconditioning in the transient cerebral ischemic rat model. CNS Neurosci Ther. Dec. 2012;18(12):965-73. doi: 10.1111/cns.12016.

Rahman et al., Remote ischemic preconditioning in human coronary artery bypass surgery: from promise to disappointment? Circulation. 2010;122:S53-59.

Ravio et al., Effect of remote ischemic conditioning on dendritic cell number in blood after renal transplantation—flow cytometry in a porcine model. Transpl Immunol. Mar. 2012;26(2-3):146-50. doi: 10.1016/j.trim.2011.10.006. Epub Nov. 4, 2011. Abstract only.

Redington et al., Exploring remote ischaemic preconditioning. Internal Innovation: 42-44. www.research.media.eu.

Ren et al., Limb remote ischemic postconditioning protects against focal ischemia in rats. Brain Res. Sep. 8, 2009;1288:88-94. doi: 10.1016/j.brainres.2009.07.029. Epub Jul. 23, 2009.

Ren et al., Limb remote-preconditioning protects against focal ischemia in rats and contradicts the dogma of therapeutic time windows for preconditioning. Neuroscience. Feb. 19, 2008;151(4):1099-103. Epub Dec. 15, 2007.

Rentoukas et al., Cardioprotective role of remote ischemic periconditioning in primary percutaneous coronary intervention: enhancement by opioid action. JACC Cardiovasc Interv. Jan. 2010;(3)(1):49-55.

Rohailla et al., Acute, delayed and chronic remote ischemic conditioning is associated with downregulation of mTOR and enhanced autophagy signaling. PLoS One. Oct. 27, 2014;9(10):e111291. doi: 10.1371/journal.pone.0111291. eCollection 2014.

Saxena et al., Remote ischemic conditioning: evolution of the concept, mechanisms, and clinical application. J Card Surg. Jan.-Feb. 2010;25(1):127-34. Epub Jun. 22, 2009.

Schipke et al., [Postconditioning: a brief review]. Herz. Sep. 2006;31(6):600-6. Review. German. Abstract.

Schmidt et al., Intermittent peripheral tissue ischemia during coronary ischemia reduces myocardial infarction through a KATP-dependent mechanism: first demonstration of remote ischemic perconditioning. Am J Physiol Heart Circ Physiol. Apr. 2007;292(4):H1883-90. Epub Dec. 15, 2006.

Schoemaker et al., Bradykinin mediates cardiac preconditioning at a distance. Am J Physiol Heart Circ Physiol. May 2000;278(5):H1571-6.

Sheng et al., Autophagy activation is associated with neuroprotection in a rat model of focal cerebral ischemic preconditioning. Autophagy. May 2010;6(4):482-94. doi: 10.4161/auto.6.4.11737. Epub May 16, 2010.

Sherwood, Chapter 10: Blood Vessels and Blood Pressure. Human Physiology: From Cells to Systems. 7th Ed. Brooks/Cole. 2008.

Shimizu et al., Effects of intermittent lower limb ischaemia on coronary blood flow and coronary resistance in pigs. Acta Physiol (Oxf). Jun. 2007;190(2):103-9. Epub Mar. 30, 2007.

Shimizu et al., Remote ischemic preconditioning decreases adhesion and selectively modifies functional responses of human neutrophils. J Surg Res. Jan. 2010;158(1):155-61.

(56) References Cited

OTHER PUBLICATIONS

Shimizu et al., Transient limb ischaemia remotely preconditions through a humoral mechanism acting directly on the myocardium: evidence suggesting cross-species protection. Clin Sci (Lond). Aug. 3, 2009;117(5):191-200.

Slepian et al., Pre-conditioning of smooth muscle cells via induction of the heat shock response limits proliferation following mechanical injury. Biochem Biophys Res Commun. Aug. 14, 1996;225(2):600-7.

Sloth et al., Improved long-term clinical outcomes in patients with ST-elevation myocardial infarction undergoing remote ischaemic conditioning as an adjunct to primary percutaneous coronary intervention. Eur Heart J. Jan. 2014;35(3):168-75. doi: 10.1093/eurheartj/eht369. Epub Sep. 12, 2013.

Sloth et al., Remote ischemic perconditioning improves long-term clinical outcome in patients undergoing primary percutaneous coronary intervention for St-Elevation myocardial infarction. J Amer Coll Cardiol. Oct. 23, 2012;60(17):B20. Abstract TCT-63.

Soendergaard et al. Improved GFR and renal plasma perfusion following remote ischaemic conditioning in a porcine kidney transplantation model. Transpl Int. Sep. 2012;25(9):1002-12. doi: 10.1111/j.1432-2277.2012.01522.x. Epub Jul. 6, 2012.

Spargias et al., beta blocker treatment and other prognostic variables in patients with clinical evidence of heart failure after acute myocardial infarction: evidence from the Aire study. Heart. Jan. 1999;81(1):25-32.

Steensrud et al., Pretreatment with the nitric oxide donor SNAP or nerve transection blocks humoral preconditioning by remote limb ischemia or intra-arterial adenosine. Am J Physiol Heart Circ Physiol. Nov. 2010;299(5):H1598-603. doi:10.1152/ajpheart.00396.2010. Epub Aug. 27, 2010.

Sun et al., Postconditioning attenuates cardiomyocyte apoptosis via inhibition of JNK and p38 mitogen-activated protein kinase signaling pathways. Apoptosis. Sep. 2006;11(9):1583-93.

Takano et al., Late preconditioning enhances recovery of myocardial function after infarction in conscious rabbits. Am J Physiol Heart Circ Physiol. Nov. 2000;279(5):H2372-81.

Takarada et al., Applications of vascular occlusion diminish disuse atrophy of knee extensor muscles. Med Sci Sports Exerc. Dec. 2000;32(12):2035-9.

Tan et al., Late phase of remote ischemic preconditioning. Chongqing Medicine. Aug. 31, 2007;36(16):1608 and 1610. Chinese.

Tanaka et al., Expression of heat shock protein after ischemic preconditioning in rabbit hearts. Jpn Circ J. Jul. 1998;62(7):512-6.

Tejwani NC et al., "Tourniquet Cuff Pressure: The Gulf Between Science and Practice," J. Trauma, 61 (6), pp. 1415-1418, Dec. 2006. Abstract only.

Thielmann et al., Remote ischemic preconditioning reduces myocardial injury after coronary artery bypass surgery with crystalloid cardioplegic arrest. Basic Res Cardiol. Sep. 2010;105(5):657-64. Epub May 21, 2010.

Thielmann et al., Remote ischemic preconditioning: the surgeon's perspective. J Cardiovasc Med (Hagerstown). Oct. 1, 2012;13:1-6 [Epub ahead of print].

Thijssen et al., Assessment of flow-mediated dilation in humans: a methodological and physiological guideline. Am J Physiol Heart Circ Physiol. Jan. 2011;300(1):H2-12. doi: 10.1152/ajpheart.00471.2010. Epub Oct. 15, 2010.

Thuny et al., Post-conditioning reduces infarct size and edema in patients with ST-segment elevation myocardial infarction. J Am Coll Cardiol. Jun. 12, 2012;59(24):2175-81.

Toledo-Pereyra et al., Molecular signaling pathways in ischemia/reperfusion. Exp Clin Transplant. Jun. 2004;2(1):174-7.

Tomai et al., Ischemic preconditioning in humans: models, mediators, and clinical relevance. Circulation. Aug. 3, 1999;100(5):559-63.

Venugopal et al., Remote ischaemic preconditioning reduces myocardial injury in patients undergoing cardiac surgery with cold-blood cardioplegia: a randomised controlled trial. Heart. Oct. 2009;95(19):1567-71. Epub Jun. 8, 2009.

Venugopal et al., Effect of remote ischemic preconditioning on acute kidney injury in nondiabetic patients undergoing coronary artery bypass graft surgery: a secondary analysis of 2 small randomized trials. Am J Kidney Dis. Dec. 2010; 5(6): 1043-9.

Vinten-Johansen et al., Postconditioning—A new link in nature's armor against myocardial ischemia-reperfusion injury. Basic Res Cardiol. Jul. 2005;100(4):295-310. Epub Mar. 30, 2005.

Wagner et al., Myocardial injury is decreased by late remote ischaemic preconditioning and aggravated by tramadol in patients undergoing cardiac surgery: a randomised controlled trial. Interact Cardiovasc Thorac Surg. Dec. 2010;11(6):758-62. doi: 10.1510/icvts.2010.243600. Epub Sep. 16, 2010.

Walsh et al., Remote ischemic preconditioning for renal and cardiac protection during endovascular aneurysm repair: a randomized controlled trial. J Endovasc Ther. Dec. 2009;16(6):680-9.

Wang et al., Remote ischemic preconditioning by hindlimb occlusion prevents liver ischemic/reperfusion injury: the role of High Mobility Group—Box 1. Ann Surg. Feb. 2010;251(2):292-9. doi: 10.1097/SLA.0b013e3181bfda8c.

Wang et al., Remote Ischemic Preconditioning Protects against Liver Ischemia-Reperfusion Injury via Heme Oxygenase-1-Induced Autophagy. PLoS One. Jun. 10, 2014;9(6):e98834. doi 10.1371/journal.pone.0098834. eCollection 2014. 12 pages.

Warzecha et al., Ischaemic preconditioning of the hundlimb or kidney does not attenuate the severity of acute ischemia/reperfusion-induced pancreaitis in rats. J Physiol Pharmacol. Jun. 2008;59(2):337-52.

Wei et al., Repeated remote ischemic postconditioning protects against adverse left ventricular remodeling and improves survival in a rat model of myocardial infarction. Circ Res. May 13, 2011;108(10):1220-5. Epub Apr. 7, 2011. Supplemental Information Included.

Whittaker et al., Remote-conditioning ischemia provides a potential approach to mitigate contrast medium-induced reduction in kidney function: a retrospective observational cohort study. Cardiology. 2011;119(3):145-50. doi: 10.1159/000330930. Epub Sep. 23, 2011.

Wolfrum et al., Calcitonin gene related peptide mediates cardioprotection by remote preconditioning. Regul Pept. Apr. 15, 2005;127(1-3):217-24.

Xie et al., Remote ischaemic preconditioning reduces myocardial injury in patients undergoing heart valve surgery: randomised controlled trial. Heart. Mar. 2012;98(5):384-8. Epub Nov. 22, 2011.

Xin et al., Combined local ischemic postconditioning and remote perconditioning recapitulate cardioprotective effects of local ischemic preconditioning. Am J Physiol Heart Circ Physiol. Jun. 2010;298(6):H1819-31. Epub Mar. 5, 2010. Erratum in: Am JPhysiolHeart Circ Physiol. Sep. 2010;299(3):H957.

Yan et al., The protective roles of autophagy in ischemic preconditioning. Acta Pharmacol Sin. May 2013;34(5):636-43. doi: 10.1038/aps.2013.18. Epub Apr. 22, 2013.

Yellon et al., Preconditioning the myocardium: from cellular physiology to clinical cardiology. Physiol Rev. Oct. 2003;83(4):1113-51.

Zhang et al., [Correlation of limb and myocardial ischemia postconditioning with acute myocardial reperfusion injury]. Zhonghua Yi Xue Za Zhi. Mar. 28, 2006;86(12):841-5. Chinese. (Abstract Only).

Zhao et al., Inhibition of myocardial injury by ischemic postconditioning during reperfusion: comparison with ischemic preconditioning. Am J Physiol Heart Circ Physiol. Aug. 2003;285(2):H579-88.

Zhao, Ischemic postconditioning as a novel avenue to protect against brain injury after stroke. J Cereb Blood Flow Metab. May 2009;29(5):873-85. doi: 10.1038/jcbfm.2009.13. Epub Feb. 25, 2009.

Zhou et al., Limb ischemic preconditioning reduces heart and lung injury after an open heart operation in infants. Pediatr Cardiol. Jan. 2010;31(1):22-9. Epub Sep. 29, 2009.

Zimmerman et al., Ischemic preconditioning at a remote site prevents acute kidney injury in patients following cardiac surgery. Kidney Int. 2011;80:861-867.

Zografos et al., Remote ischemic preconditioning reduces peri-procedural myocardial injury in elective percutaneous coronary

(56) References Cited

OTHER PUBLICATIONS intervention: a meta-analysis. Int J Cardiol. May 15, 2014;173(3):530-2. doi: 10.1016/j.ijcard.2014.03.026. Epub Mar. 15, 2014.

* cited by examiner

METHODS FOR MODULATING AUTOPHAGY USING REMOTE ISCHEMIC CONDITIONING

RELATED CASE INFORMATION

The present application is a national stage filing under 35 U.S.C. 371 of International Application No. PCT/IB2014/001426, filed Mar. 14, 2014, which claims priority to U.S. Provisional Application No. 61/798,622, filed Mar. 15, 2013, both of which are incorporated herein by reference in their entirety.

RELATED APPLICATIONS

This application claims the benefit under 35 U.S.C. § 119(e) of U.S. Provisional Application No. 61/798,622, filed Mar. 15, 2013, and entitled "METHODS FOR MODULATING AUTOPHAGY USING REMOTE ISCHEMIC CONDITIONING," the entire contents of which are incorporated herein by reference.

FIELD OF THE INVENTION

The invention provides methods and compositions for treatment of various conditions using ischemic conditioning.

SUMMARY OF INVENTION

Remote ischemic conditioning (RIC) has a beneficial effect on human diseases involving ischemia and reperfusion injury. These effects are believed to be mediated, in part, by direct cellular activation of pro-survival pathways. These effects are also believed to be mediated, in part, by modification of the ischemic milleu, including modification of cytokine and pro-inflammatory markers, blood vessel function, platelet function, and neutrophil function.

The chronic use of RIC strategies to modify particular human disease has been reported in the context of modification of remodelling after myocardial infarction presumably mediated by anti-inflammatory factors, long-term outcomes showing reduction of recurrent stroke after an initial embolic stroke event, and reduction in morbidity and mortality when RIC is used at the time of cardiovascular surgery or other interventions.

The invention is based, in part, on the unexpected and surprising finding that RIC, including chronic RIC, modifies autophagy. Autophagy is involved in a number of abnormal processes associated with cancer, metabolic and neurodegenerative disorders, and cardiovascular and pulmonary diseases. Autophagy also plays a role in the response to exercise and in aging. In accordance with the invention, it has been found that RIC modulates, and more specifically increases, autophagy signaling within the heart and other organs. This finding indicates that RIC may be used prophylactically and/or therapeutically in the context of conditions that, heretofore, have not been contemplated to benefit from RIC. Such conditions include but are not limited to cancer, metabolic disorders, neurodegenerative disorders, pulmonary diseases, and aging generally.

Thus, in one aspect, the invention provides a method comprising performing remote ischemic conditioning (RIC) or a RIC-like intervention on a subject having or at risk of developing a condition that benefits from enhanced autophagy.

In some embodiments, the subject has a condition that benefits from enhanced autophagy.

In some embodiments, the condition that benefits from enhanced autophagy is cancer. In some embodiments, the condition that benefits from enhanced autophagy is B cell lymphoma, skin cancer, melanoma, basal cell carcinoma, liver cancer, small cell lung cancer, or small cell lung cancer.

In some embodiments, the condition that benefits from enhanced autophagy is a neurodegenerative disease. In some embodiments, the condition that benefits from enhanced autophagy is Alzheimer's disease, Huntington's disease, multiple sclerosis, or Parkinson's disease.

In some embodiments, the condition that benefits from enhanced autophagy is an infectious disease. In some embodiments, the condition that benefits from enhanced autophagy is a *Mycobacteria* spp infection, a *M. tuberculosis* infection, a *M. avium* infection, a *M. intracellulare* infection, a *M. kansaii* infection, a *M. gordonae* infection, a *Shigella flexneri* infection, a *Salmonella enterica* infection, a *Listeria monocytogenes* infection, or a *Francisella tularensis* infection.

In some embodiments, the condition that benefits from enhanced autophagy is a gastrointestinal condition. In some embodiments, the condition that benefits from enhanced autophagy is Crohn's disease or ulcerative colitis.

In some embodiments, the condition that benefits from enhanced autophagy is an autoimmune condition. In some embodiments, the condition that benefits from enhanced autophagy is rheumatoid arthritis, juvenile rheumatoid arthritis, systemic lupus erythematosus (SLE), lupus nephritis, ulcerative colitis, Wegener's disease, inflammatory bowel disease, idiopathic thrombocytopenic purpura (ITP), thrombotic thrombocytopenic purpura (TTP) autoimmune thrombocytopenia multiple sclerosis psoriasis. IgA nephropathy, IgM polyneuropathies, myasthenia gravis, vasculitis, diabetes mellitus, Reynaud's syndrome, Sjorgen's syndrome and glomerulonephritis.

In some embodiments, the condition that benefits from enhanced autophagy is a cardiovascular disease. In some embodiments, the condition that benefits from enhanced autophagy is atherosclerosis, arteriosclerosis, cardiomyopathy or cardiac hypertrophy.

In some embodiments, the condition that benefits from enhanced autophagy is a genetic x-linked lysosome associated membrane protein diseases, Danon's disease, a mitochondrial myopathy, or chronic myocarditis.

In some embodiments, the condition that benefits from enhanced autophagy is diabetes, obesity, metabolic syndrome, glucose intolerance, hyperlipidemia, or hypercholesterolemia.

In some embodiments, the condition that benefits from enhanced autophagy is a pulmonary disease. In some embodiments, the condition that benefits from enhanced autophagy is chronic obstructive pulmonary disease, cystic fibrosis, emphysema, asthma, pulmonary hypertension, or idiopathic pulmonary fibrosis.

In some embodiments, RIC is performed on the subject. In some embodiments, the RIC is chronic RIC. In some embodiments, the RIC is acute RIC. In some embodiments, RIC is performed on a daily basis. In some embodiments, RIC is performed more than once a day.

In some embodiments, RIC is performed on at least a daily basis for at least one month, two months, three months, four months, five months, six months, seven months, eight months, nine months, ten months, eleven months, or a year.

In some embodiments, RIC is performed every other day for at least one month, two months, three months, four months, five months, six months, seven months, eight months, nine months, ten months, eleven months, or a year.

In some embodiments, RIC comprises 1, 2, 3, 4, 5 or more cycles, each cycle comprising a blood occlusion period and a reperfusion period. In some embodiments, RIC comprises one or more cycles, each cycle comprising a 5 minute blood occlusion period and a 5 minute reperfusion period.

In some embodiments, RIC is performed repeatedly at the same site. In some embodiments, RIC is performed repeatedly on an upper limb. In some embodiments, RIC is performed repeatedly on a lower limb. In some embodiments RIC is performed on one or more limbs, including one or both arms, one or both legs, and one or both arms and one or both legs.

In some embodiments, the RIC-like intervention is performed on the subject. In some embodiments, the RIC-like intervention is non-invasive electrical nerve stimulation. In some embodiments, RIC and the RIC-like intervention, such as but not limited to non-invasive electrical nerve stimulation, are both performed on the subject.

In some embodiments, the subject is receiving a second therapy. In some embodiments, the second therapy is administered at less than a maximum tolerable dose. In some embodiments, the second therapy is administered at greater than the maximum tolerable dose.

These and other aspects and embodiments of the invention will be discussed in greater detail herein.

DETAILED DESCRIPTION OF INVENTION

Figure 1:
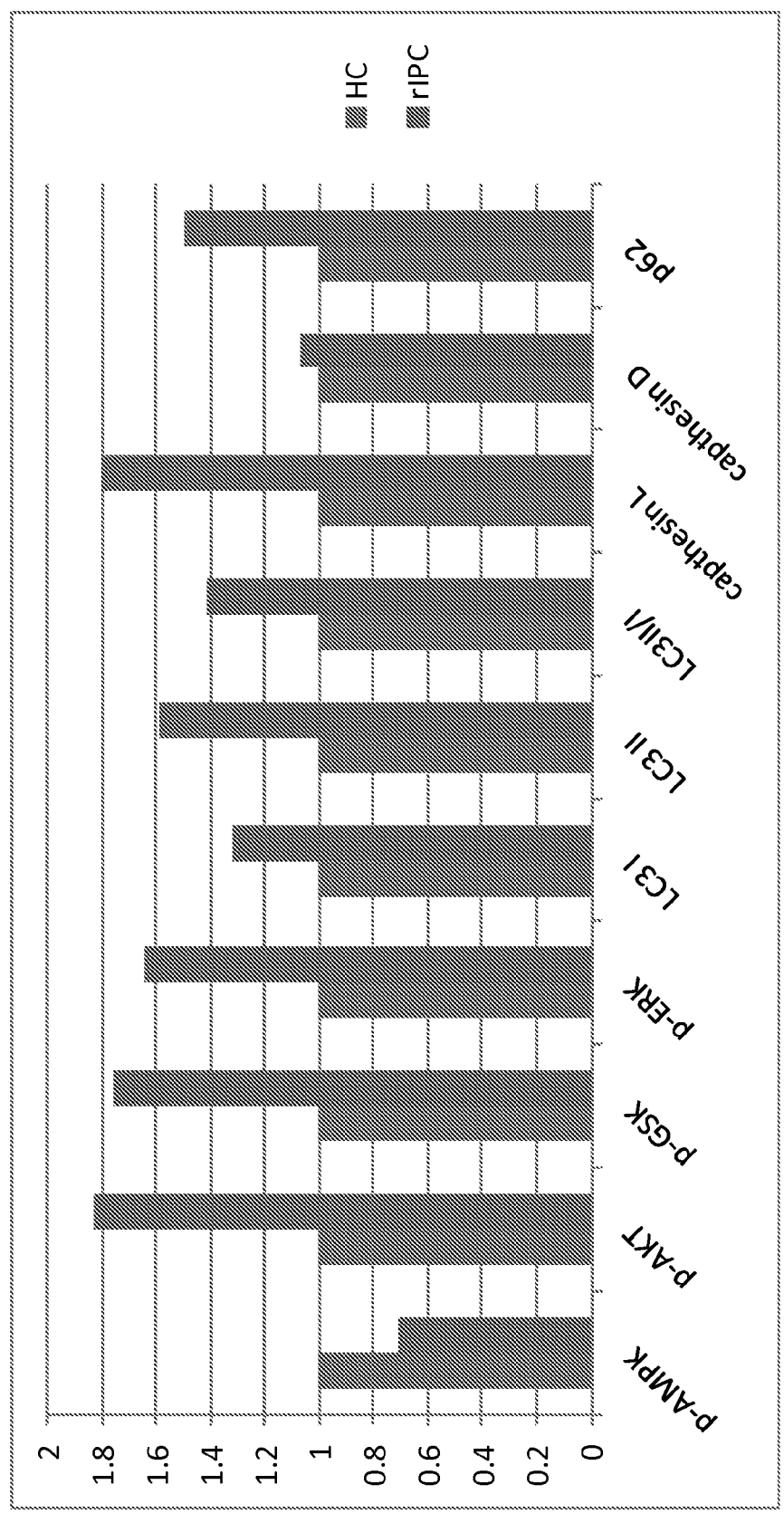
FIG. 1. Cellular expression of autophagy protein markers measured in myocardium of mice after 10 days of RIC as compared to untreated controls. The markers from left to right are p-AMPK, p-AKT, p-GSK, p-ERK, LC3 I, LC3 II, LC3 II/I, capthesin L, capthesin D, and p62.

The invention contemplates new uses for remote ischemic conditioning (RIC) including chronic RIC based on the unexpected discovery that RIC upregulates and/or enhances autophagy and its related inflammatory signaling pathways and enhance the autophagy mechanism. This finding indicates that RIC may be used as a prophylactic and/or therapeutic for a number of select conditions, the origins of which, and their response to treatment, and/or outcomes have an underlying autophagy component. The invention further contemplates directly limiting adverse inflammatory, fibrotic, and remodeling and oncogenic signals in cells or tissues that are subject to such conditions.

Heretofore, RIC has been contemplated primarily for use in the treatment of ischemic and/or reperfusion injury. Thus, RIC has been contemplated for use primarily for myocardial infarction and ensuing heart failure, restenosis, and traumatic injury including trauma associated with hypovolemic shock. RIC has also been contemplated as an adjunct to surgery such as cardiovascular surgery. RIC has also been reported to provide performance enhancement to healthy subjects including elite swimmers as well as subjects having conditions that impair exercise (e.g., cardiovascular disease). In some instances, the subjects to be treated according to the invention may be subjects that would not have been previously contemplated for RIC therapy.

Given the emphasis on the beneficial effects of RIC on conditions having an underlying ischemia/reperfusion injury, it is surprising that RIC would have beneficial effects in other conditions in which ischemia/reperfusion injury is not known to play a significant role, if any.

The invention therefore contemplates using RIC in subjects having reduced autophagy activity in order to induce or increase autophagy activity (or to enhance endogenous autophagy levels) in the subject. The invention also contemplates using RIC in subjects having discernable (e.g., detectable) autophagy activity in order to increase autophagy activity in the subject. These effects may be direct effects on the cell, or they of circulating or local micro-RNA that are able to affect disease via direct effects on autophagy, or on the disease process itself. Thus, RIC may be able to modify cancer progression at early and/or late stages, including metastasis, via either a direct or an indirect mechanism.

Autophagy refers to a process that involves degradation of cellular components via lysosomal mechanisms. Autophagy includes microautophagy, macroautophagy, and chaperone-mediated autophagy. The major form of autophagy is macroautophagy. Macroautophagy is a process that involves compartmentalization of cytoplasmic components into double membrane (e.g., lipid bilayers) structures referred to as autophagosomes. These autophagosomes merge (or fuse) with lysosomes and their contents are then degraded and recycled. Microautophagy does not use the autophagosome intermediate and instead involves the direct engulfment of cellular components into lysosomes through invagination of the lysosome membrane. Chaperone-mediated autophagy involves chaperones such as heat-shock proteins to facilitate transfer of the cellular components (including proteins) to lysosomes.

Autophagy activity in a subject can be measured by the presence of one or more autophagy markers. In some embodiments, more than one marker is measured, including 2, 3, 4, 5, 6, 7, 8, 9, 10 or more markers. Examples of autophagy markers include but are not limited to p-AMPK, p-AKT, p-GSK, p-ERK, LC3I, LC3II, LC3II/I, capthesin L, capthesin D and p62. The "p-" prefix denotes the phosphorylated form of the protein marker. This does not apply to p62, as will be understood in the art. AMPK (adenosine 5' monophosphate-activated protein kinase) is a positive regulator of autophagy. It responds to energy depletion (e.g., in the form of AMP accumulation). Activation of AMPK negatively regulates mTOR (mammalian target of rapamycin) complex 1. Other autophagy markers include but are not limited to mTOR and Beclin. Thus, modulation of autophagy by RIC can also be measured by effect on mTOR and Beclin, as well in some instances.

Reference can be made to Choi et al. N Engl J Med 368(7): 651 (2013) for a discussion and overview of autophagy. This reference is incorporated by reference herein in its entirety.

Enhanced autophagy, as used herein, intends an increase in the expression level of one or more autophagy markers (such as those provided herein) or an increase in the activity level of one or more autophagy markers (such as those provided herein). In some embodiments, an increased expression level or the activity level is relative to control or is relative to pre-RIC level or activity. Methods for measuring expression levels, whether mRNA or protein expression levels, are known in the art.

The invention contemplates treating subjects using RIC and/or a RIC-like intervention alone or in combination with one or more other therapies used for such conditions, examples of which are provided herein. RIC may be performed chronically (chronic RIC) or it may performed acutely (acute RIC).

The invention contemplates treating subjects having or at risk of developing any of the conditions recited herein. Subjects at risk of developing one (or more) of these conditions may be at risk due to family history (where a genetic inheritable component has been recognized), or due to exposure to one or more agents, or due to lifestyle and environment.

A subject includes but is not limited to humans and other non-human animals including, for example, companion animals such as dogs, cats, domesticated pigs, ferrets, hamsters, and the like; primates such as monkeys, and the like; agricultural animals such as cattle, pigs, horses, sheep, goats, birds (e.g., chickens, ducks, geese, and/or turkeys); prize-winning animals such as thoroughbreds, and the like. In important embodiments, the subject is a human subject.

In some instances, the subjects may not be experiencing, have experienced or be at risk of experiencing a myocardial infarction, or a restenotic event, or a traumatic injury.

Generally, to treat, as used herein, encompasses to prevent, to delay, or to ameliorate, as appropriate, development or continuance or aggravation of a condition in a subject or to relieve, reduce or alleviate at least one symptom of a condition. For example, treatment can be diminishment of one or several symptoms of such a condition or complete eradication of the condition. Within the meaning of the present invention, the term treat also denotes to arrest, delay the onset (i.e., the period prior to clinical manifestation of a condition) and/or reduce the risk of developing or worsening a condition.

Conditions to be treated using RIC (acute or chronic) and/or RIC-like intervention include but are not limited to cancer neurodegenerative diseases infectious diseases, and chronic gastrointestinal diseases. Various of these conditions have been reported to benefit from autophagic mechanism(s). As an example, it has been reported that suppression of autophagy is associated with increased malignant potential in the case of cancer. It has also been reported that enhanced autophagy can suppress cancer growth. Examples of such cancers include but are not limited to B cell lymphoma, skin cancer such as melanoma, liver cancer, and lung cancer. It has not been known heretofore however that RIC can promote or enhance autophagy. Thus, the invention contemplates use of RIC to promote or enhance autophagy in a variety of subjects having or at risk of developing conditions that are susceptible to enhanced autophagy. RIC may affect these various conditions through direct or indirect mechanisms, including but not limited to inducing increases in the levels of circulating or local micro-RNA that in turn are able to affect the condition. Such conditions include but are not limited to cancer including metastasis.

Remote Ischemic Conditioning (RIC)

Remote ischemic conditioning (RIC), as used herein, refers to a non-invasive process of deliberately inducing an ischemic event or period (typically by occluding arterial blood flow) followed by a reperfusion event or period (typically where blood is allowed to reperfuse) that is typically performed on an upper or lower limb or on a region of the body that is remote from an organ or tissue that is intended to benefit from the process itself.

RIC may be performed as a single cycle (i.e., one ischemic event followed by one reperfusion event) or as multiple cycles. Multiple cycles include but are not limited to two, three, four, five or more cycles. The one or multiple cycles, when performed consecutively without significant delay, are referred to a RIC regimen or treatment.

The blood flow restriction (or occlusion) typically takes the form of an applied pressure to the limb that is sufficient to occlude blood through the limb. In some instances, the occlusive blood pressure is above systolic pressure (i.e., supra-systolic pressure). It may be about 5, about 10, about 15, about 20, or more mmHg above (or greater than) systolic pressure. In some instances, the occlusive blood pressure may be at or below systolic pressure. Since systolic pressure will differ between subjects, the absolute pressure needed to induce ischemia will vary between subjects. In other embodiments the pressure may be preset at, for example, 200 mmHg. The blood flow restriction may be accomplished using any method or device provided it is capable of inducing transient ischemia and reperfusion, whether manually or automatically. Such devices include without limitation a manually inflatable cuff, or an automated device as described below. The devices comprise cuffs of standard width or cuffs of greater than standard width.

The induced ischemic event or period is transient. That is, it may have a duration of about 1, about 2, about 3, about 4, about 5, or more minutes. Similarly, the reperfusion event or period may have a duration of about 1, about 2, about 3, about 4, about 5, or more minutes.

One or both upper limbs or one or both lower limbs may be used although in some instances one or both upper limbs are preferred. In some instances, RIC is performed on two different sites on the body, in an overlapping or simultaneous manner.

Devices for performing RIC are also known in the art, and include those described in U.S. Pat. No. 7,717,855 and US patent application publication 2012/0265240 A1, both of which are incorporated herein by reference in their entirety. Briefly, this system comprises a cuff configured to retract about a limb of a subject, an actuator connected to the cuff that when actuated causes the cuff to contract about the limb of the subject to reduce blood flow therethrough, and a controller that controls the actuator according to a treatment protocol. The treatment protocol typically includes a plurality of treatment cycles, each of which may comprise a cuff actuation period during which the actuator contracts the cuff about the limb of the subject to a pressure that occludes blood flow through the limb, an ischemic duration period during which the actuator maintains the cuff contracted about the limb at a set pressure point to occlude blood flow through the limb, a cuff release period during which the actuator releases the cuff to allow blood flow through the limb, and a reperfusion period during which the cuff is maintained about the limb in a relaxed state to allow blood flow through the limb.

Chronic RIC

The invention contemplates treating various conditions and diseases recited herein using chronic RIC. As used herein, chronic RIC means performing a RIC regimen (which itself may comprise 1, 2, 3, 4, 5 or more cycles of ischemia and reperfusion) more than once over the course of more than one day. Chronic RIC encompasses daily performance of a RIC regimen, weekly performance of a RIC regimen, bi-weekly performance of a RIC regimen, monthly performance of a RIC regimen, including performance that is more or less frequent. Chronic RIC also encompasses performing a RIC regimen every other day, every third day, every fourth day, every fifth day, or every sixth day. The RIC regimens may be identical to each other or they may differ. Chronic RIC encompasses scheduled RIC regimens (e.g., non-random RIC regimens) or random RIC regimens (e.g., performing RIC when a subject feels the need rather than on a set schedule). Chronic RIC also contemplates that more than one RIC regimen may be performed on a single day.

RIC-Like Interventions

RIC-like interventions include but are not limited to non-invasive electrical nerve stimulation such as transcutaneous electrical nerve stimulation, direct nerve stimulation such as femoral nerve stimulation, electro-acupuncture, nociceptive c-fiber stimulation for example via topical capsaicin, and intra-arterial adenosine.

As used herein, non-invasive electrical nerve stimulation may be a single cycle of nerve stimulation followed by a rest period during which no current is applied to the subject, or it may be repeated cycles of nerve stimulation followed by a rest period. The repeated cycles may comprise 2, 3, 4, 5 or more cycles of nerve stimulation followed by a rest period. For clarity, two cycles of non-invasive electrical nerve stimulation would consist of a nerve stimulation period, a rest period, a nerve stimulation period, and a rest period. The invention contemplates that, in some embodiments, a single nerve stimulation period may be sufficient to achieve the desired therapeutic, prophylactic or performance endpoints.

The nerve stimulation period and the rest period may each range from 30 seconds to several minutes or hours. Either or both periods may be up to or about 30 seconds, or 1, 2, 3, 4, 5, 6, 7, 8, 9, 10, 15, 20, 25, 30, 35, 40, 45, 50, 55 or 60 minutes in duration, or longer. The two periods may or may not be of the same duration. An exemplary non-invasive electric nerve stimulation comprises 4 or 5 cycles of 5 minutes of nerve stimulation followed by 5 minutes of rest. Another exemplary non-invasive electrical nerve stimulation comprises 4 or 5 cycles of 4 minutes of nerve stimulation followed by 4 minutes of rest.

The non-invasive electrical nerve stimulation device may be operated under any number of pulse amplitude (or intensity), pulse width, and pulse frequency settings. As an example, the pulse amplitude may range from 1 to 200 mA, including typically from 1 to 100 mA, from 1 to 90 mA, from 1-80 mA, from 1-70 mA, from 1-60 mA, from 1-50 mA, from 1-40 mA, from 1-30 mA, from 1-20 mA, from 1-15 mA, from 1-10 mA, from 1-9 mA, from 1-8 mA, from 1-7 mA, from 1-6 mA, from 1-5 mA, from 1-4 mA, from 1-3 mA, or from 1-2 mA. The pulse frequency may range from 1 to 300 Hz, including typically from 1 to 150 Hz, from 1-140 Hz, from 1-130 Hz, from 1-120 Hz, from 1-110 Hz, from 1-100 Hz, from 1-90 Hz, from 1-80 Hz, from 1-70 Hz, from 1-60 Hz, from 1-50 Hz, from 1-40 Hz, from 1-30 Hz, from 1-20 Hz, from 1-10 Hz, from 1-9 Hz, from 1-8 Hz, from 1-7 Hz, from 1-6 Hz, from 1-5 Hz, from 1-4 Hz, from 1-3 Hz, or from 1-2 Hz. The pulse width may range up to 1 to 1600 microseconds, including typically from 1 to 800 microseconds, from 1-700 milliseconds, from 1-600 milliseconds, from 1-500 milliseconds, from 1-400 milliseconds, from 1-300 milliseconds, from 1-200 milliseconds, from 1-100 milliseconds, and from 1-50 milliseconds. The device may also operate at a voltage typically up to 80 V, including typically up to 40 V, up to 30 V, up to 20 V, up to 10 V, and up to 5 V. Exemplary settings include a pulse amplitude of 2-3 mA, a pulse frequency of 3.1 Hz, and a pulse width of 500 microseconds.

Non-invasive electrical nerve stimulation may be performed at any site on the body that is amenable to the non-invasive procedure. It may be performed on any outer surface of the body, including but not limited to arms, legs, feet, hands, torso, chest, back, and the like. It may be performed at a remote site (i.e., a site that is distal to the area of the body experiencing or likely to experience the ischemic and/or reperfusion injury). In other words, the placement of the electrodes may be distal to the region of the body being treated. As an example, the electrodes may be placed on the legs in order to reduce injury in the heart. Typically at least two electrodes are placed within proximity of each other in order to allow current to flow therebetween. Additional paired electrodes may be used at the same or different surface region of the body at the same or different time.

Repeated non-invasive electrical nerve stimulations may be performed at a single, identical site or at multiple, different sites on the body. As an example, a first stimulation may be performed on the right upper arm, followed by a second stimulation performed on the left upper arm. In some embodiments, the non-invasive electrical nerve stimulation is not performed on the chest. Repeated non-invasive electrical nerve stimulations may alternate between two sites or they may cycle through more than two sites. In some instances, non-invasive electrical nerve stimulation may be performed on a subject at two different sites at overlapping times including simultaneously. The use of more than one location may be determined a priori or it may be random. When multiple locations are used simultaneously, one or more devices may be used.

Cancers

Cancers to be treated with RIC and/or a RIC-like intervention include but are not limited to basal cell carcinoma, biliary tract cancer; bladder cancer; bone cancer; brain cancer; breast cancer; cervical cancer; choriocarcinoma; CNS cancer; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; acute myeloid leukemia; acute lymphoid leukemia, chronic myeloid leukemia, chronic lymphoid leukemia, leukemia, liver cancer; small cell lung cancer; non-small cell lung cancer; lymphoma, Hodgkin's lymphoma; Non-Hodgkin's lymphoma; melanoma; myeloma; neuroblastoma; oral cavity cancer; ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; and cancer of the urinary system.

In another embodiment, the cancer is selected from the group consisting of bladder cancer, breast cancer, colon cancer, endometrial cancer, head and neck cancer, leukemia, lung cancer, lymphoma, melanoma, ovarian cancer, prostate cancer and rectal cancer.

In another embodiment, the cancer is a refractory cancer. Examples of refractory cancers include but are not limited to leukemias, melanomas, renal cell carcinomas, colon cancer, liver (hepatic) cancers, pancreatic cancer, Non-Hodgkin's lymphoma, and In still another embodiment, the cancer is a metastasis.

Neurodegenerative Diseases

Neurodegenerative diseases to be treated with RIC and/or a RIC-like intervention include but are not limited to Alzheimer's disease, Huntington's disease, multiple sclerosis, and Parkinson's disease.

Infectious Diseases

Infectious diseases may be treated with RIC and/or a RIC-like intervention. The infectious disease may be selected from the group consisting of a bacterial infection, a mycobacterial infection, a viral infection, a fungal infection and a parasitic infection, but it is not so limited.

In one embodiment, the bacterial infection is selected from the group consisting of an *E. coli* infection, a Staphylococcal infection, a Streptococcal infection, a *Pseudomonas* infection, *Clostridium difficile* infection, *Legionella* infection, *Pneumococcus* infection, *Haemophilus* infection, *Klebsiella* infection, *Enterobacter* infection, *Citrobacter* infection, *Neisseria* infection, *Shigella* infection, *Salmonella* infection, *Listeria* infection, *Pasteurella* infection, *Streptobacillus* infection, *Spirillum* infection, *Treponema* infection, *Actinomyces* infection, *Borrelia* infection, *Corynebacterium* infection, *Nocardia* infection, *Gardnerella* infection, *Campylobacter* infection, *Spirochaeta* infection, *Proteus* infection, *Bacteroides* infection, *H. pylori* infection, and anthrax infection.

The mycobacterial infection may be tuberculosis or leprosy respectively caused by the *M. tuberculosis* and *M. leprae* species, but is not so limited.

In one embodiment, the viral infection is selected from the group consisting of an HIV infection, a Herpes simplex virus 1 infection, a Herpes simplex virus 2 infection, cytomegalovirus infection, hepatitis A virus infection, hepatitis B virus infection, hepatitis C virus infection, human papilloma virus infection, Epstein Barr virus infection, rotavirus infection, adenovirus infection, influenza A virus infection, respiratory syncytial virus infection, varicella-zoster virus infections, small pox infection, monkey pox infection and SARS infection.

In yet another embodiment, the fungal infection selected from the group consisting of candidiasis, ringworm, histoplasmosis, blastomycosis, paracoccidioidomycosis, cryptococcosis, aspergillosis, chromomycosis, mycetoma infections, pseudallescheriasis, and tinea versicolor infection.

In another embodiment, the parasite infection is selected from the group consisting of amebiasis, *Trypanosoma cruzi* infection, Fascioliasis, Leishmaniasis, *Plasmodium* infections, Onchocerciasis, Paragonimiasis, *Trypanosoma brucei* infection, *Pneumocystis* infection, *Trichomonas vaginalis* infection, *Taenia* infection, Hymenolepsis infection, *Echinococcus* infections, Schistosomiasis, neurocysticercosis, *Necator americanus* infection, and *Trichuris trichiura* infection.

In another embodiment, the infectious disease is an infection of a *Mycobacteria* sps (e.g. *M. tuberculosis, M. avium, M. intracellulare, M. kansaii, M. gordonae*), *Shigella flexneri, salmonella enterica, listeria monocytogenes*, and *francisella tularensis*.

Gastrointestinal Diseases

Chronic gastrointestinal diseases to be treated with RIC and/or a RIC-like intervention include but are not limited to such as inflammatory bowel disease, Crohn's disease and ulcerative colitis.

Cardiovascular Diseases

Cardiovascular diseases to be treated with RIC and/or a RIC-like intervention include cardiomyopathies, cardiac hypertrophy, ischemic heart disease, heart failure, and atherosclerosis. In some instances, the subject has not experienced a myocardial infarction and is not experiencing a myocardial infarction. In some embodiments, the subject is not and has not undergone ventricular remodeling as a result of a myocardial infarction.

Other Conditions

The invention further contemplates use of RIC and/or a RIC-like intervention in the treatment of genetic x-linked lysosome associated membrane protein diseases (Danon's disease), mitochondrial myopathies, and chronic myocarditis.

The invention further contemplates use of RIC and/or a RIC-like intervention in the treatment of metabolic diseases or conditions such as but not limited to insulin sensitivity and diabetes, obesity, metabolic syndrome, glucose intolerance, hyperlipidemia, and hypercholesterolemia.

The invention further contemplates use of RIC and/or a RIC-like intervention in the treatment of pulmonary diseases such as chronic obstructive pulmonary disease, cystic fibrosis, emphysema, asthma, pulmonary hypertension, and idiopathic pulmonary fibrosis.

The invention further contemplates use of RIC and/or a RIC-like intervention in the treatment of kidney disease.

The invention further contemplates use of RIC and/or a RIC-like intervention in the treatment of skin conditions. Examples include eczema, seborrheic dermatitis, skin cancer including non-melanoma skin cancer, basal cell carcinoma, and psoriasis.

The invention further contemplates use of RIC and/or a RIC-like intervention in the treatment of transplant rejection.

Autophagy is a key regulator of the aging process with reduced autophagy signalling associated with age dependent changes in many tissues. It has been suggested that modulation of autophagy will influence life span. Consequently, the invention further contemplates use of RIC and/or a RIC-like intervention for age-related degenerative diseases. In a similar manner, the invention contemplates use of RIC and/or a RIC-like intervention to increase life span.

RIC and RIC-Like Interventions as Adjunct Therapy or in Combination Therapy

The invention contemplates the use of RIC and/or RIC-like interventions in the treatment of conditions (including infectious diseases) that benefit from autophagy (and enhanced autophagy). RIC and/or RIC-like interventions may be used as a stand alone or in combination with another therapy. When used together with another therapy, in some instances, RIC and/or RIC-like interventions may reduce the adverse effects of the other therapy. In other instances, RIC and/or RIC-like therapy may synergize with the other therapy, resulting in a greater than additive effect when both therapies are used together (as compared to when they are used separately and thus independently). In some instances, the invention contemplates using RIC and/or RIC-like interventions with a dose of another therapy that is less than the dose that would otherwise be required if the other therapy was administered alone. Dose reductions may be 1%, 2%, 3%, 3%, 4%, 5%, 6%, 7%, 8%, 9%, 10%, 20% or more. Dose reductions can also take the form of less frequent administration of the other therapy.

Various therapies are known for the conditions provided herein and contemplated by the invention. A non-limiting list of such therapies are provided herein. It is intended that RIC and/or RIC-like interventions may be used with any of these therapies.

Anti-Microbial Therapies

Combination therapy may include antimicrobials agents if the condition is an infectious disease. Examples of anti-microbials include anti-bacterials, anti-mycobacterials, anti-virals, anti-fungal, and anti-parasites.

Examples of anti-bacterials include β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), and other β-lactams (such as imipenem, monobactams), β-lactamase inhibitors, vancomycin, aminoglycosides and spectinomycin, tetracyclines, chloramphenicol, erythromycin, lincomycin, clindamycin, rifampin, metronidazole, polymyxins, sulfonamides and trimethoprim, and quinolines.

Anti-bacterials include: Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefanarole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium;

Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin.

Anti-mycobacterials include Myambutol (Ethambutol Hydrochloride), Dapsone (4,4'-diaminodiphenylsulfone), Paser Granules (aminosalicylic acid granules), Priftin (rifapentine), Pyrazinamide, Isoniazid, Rifadin (Rifampin), Rifadin IV, Rifamate (Rifampin and Isoniazid), Rifater (Rifampin, Isoniazid, and Pyrazinamide), Streptomycin Sulfate and Trecator-SC (Ethionamide).

Anti-virals include amantidine and rimantadine, ribivarin, acyclovir, vidarabine, trifluorothymidine, ganciclovir, zidovudine, retinovir, and interferons.

Anti-virals further include: Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime and integrase inhibitors.

Anti-fungals include imidazoles and triazoles, polyene macrolide antibiotics, griseofulvin, amphotericin B, and flucytosine. Antiparasites include heavy metals, antimalarial quinolines, folate antagonists, nitroimidazoles, benzimidazoles, avermectins, praxiquantel, ornithine decarboxylase inhibitors, phenols (e.g., bithionol, niclosamide); synthetic alkaloid (e.g., dehydroemetine); piperazines (e.g., diethylcarbamazine); acetanilide (e.g., diloxanide furonate); halogenated quinolines (e.g., iodoquinol (diiodohydroxyquin)); nitrofurans (e.g., nifurtimox); diamidines (e.g., pentamidine); tetrahydropyrimidine (e.g., pyrantel pamoate); sulfated naphthylamine (e.g., suramin).

Other anti-infectives include Difloxacin Hydrochloride; Lauryl Isoquinolinium Bromide; Moxalactam Disodium; Ornidazole; Pentisomicin; Sarafloxacin Hydrochloride; Protease inhibitors of HW and other retroviruses; Integrase Inhibitors of HIV and other retroviruses; Cefaclor (Ceclor); Acyclovir (Zovirax); Norfloxacin (Noroxin); Cefoxitin (Mefoxin); Cefuroxime axetil (Ceftin); Ciprofloxacin (Cipro); Aminacrine Hydrochloride; Benzethonium Chloride: Bithionolate Sodium; Bromchlorenone; Carbamide Peroxide; Cetalkonium Chloride; Cetylpyridinium Chloride: Chlorhexidine Hydrochloride; Clioquinol; Domiphen Bromide; Fenticlor; Fludazonium Chloride; Fuchsin, Basic; Furazolidone; Gentian Violet; Halquinols; Hexachlorophene: Hydrogen Peroxide; Ichthammol; Imidecyl Iodine; Iodine; Isopropyl Alcohol; Mafenide Acetate; Meralein Sodium; Mercufenol Chloride; Mercury, Ammoniated; Methylbenzethonium Chloride; Nitrofurazone; Nitromersol; Octenidine Hydrochloride; Oxychlorosene; Oxychlorosene Sodium; Parachlorophenol, Camphorated; Potassium Permanganate; Povidone-Iodine; Sepazonium Chloride; Silver Nitrate; Sulfadiazine, Silver; Symclosene; Thimerfonate Sodium; Thimerosal: Troclosene Potassium.

Anti-Cancer Therapies

The other therapies may be anti-cancer therapies if the condition is a cancer or other condition characterized by abnormal cell proliferation. Anti-cancer therapies include chemotherapy, surgery and/or radiation.

Chemotherapeutic agents include but are not limited to those currently in use. Several chemotherapeutic agents can be categorized as DNA damaging agents and these include topoisomerase inhibitors (e.g., etoposide, ramptothecin, topotecan, teniposide, mitoxantrone), anti-microtubule agents (e.g., vincristine, vinblastine), anti-metabolic agents (e.g., cytarabine, methotrexate, hydroxyurea, 5-fluorouracil, floxuridine, 6-thioguanine, 6-mercaptopurine, fludarabine, pentostatin, chlorodeoxyadenosine), DNA alkylating agents (e.g., cisplatin, mechlorethamine, cyclophosphamide, ifosfamide, melphalan, chorambucil, busulfan, thiotepa, carmustine, lomustine, carboplatin, dacarbazine, procarbazine), DNA strand break inducing agents (e.g., bleomycin, doxorubicin, daunorubicin, idarubicin, mitomycin C), and radiation therapy.

Some chemotherapeutic agents are those selected from the group consisting of: Acivicin; Aclarubicin; Acodazole Hydrochloride; Acronine; Adozelesin; Adriamycin; Aldesleukin; Alitretinoin; Allopurinol Sodium; Altretamine; Ambomycin; Ametantrone Acetate; Aminoglutethimide; Amsacrine; Anastrozole; Annonaceous Acetogenins; Anthramycin; Asimicin; Asparaginase; Asperlin; Azacitidine; Azetepa; Azotomycin; Batimastat; Benzodepa; Bexarotene; Bicalutamide; Bisantrene Hydrochloride; Bisnafide Dimesylate; Bizelesin; Bleomycin Sulfate; Brequinar Sodium; Bropirimine; Bullatacin; Busulfan; Cabergoline; Cactinomycin; Calusterone; Caracemide; Carbetimer; Carboplatin; Carmustine; Carubicin Hydrochloride; Carzelesin; Cedefingol; Celecoxib; Chlorambucil; Cirolemycin; Cisplatin; Cladribine; Crisnatol Mesylate; Cyclophosphamide; Cytarabine; Dacarbazine; DACA (N-[2-(Dimethyl-amino)ethyl] acridine-4-carboxamide); Dactinomycin; Daunorubicin Hydrochloride; Daunomycin; Decitabine; Denileukin Diftitox; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Flurocitabine; Fosquidone; Fostriecin Sodium; FK-317; FK-973; FR-66979; FR-900482; Gemcitabine; Gemcitabine Hydrochloride; Gemtuzumab Ozogamicin; Gold Au 198; Goserelin Acetate; Guanacone; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Methoxsalen; Metoprine; Meturedepa; Mitindomide; Mitocarcin; Mitocromin; Mitogillin; Mitomalcin; Mitomycin; Mytomycin C; Mitosper; Mitotane; Mitoxantrone Hydrochloride; Mycophenolic Acid; Nocodazole; Nogalamycin; Oprelvekin; Ormaplatin; Oxisuran; Paclitaxel; Pamidronate Disodium;

Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rituximab; Rogletimide; Rolliniastatin; Safingol; Safingol Hydrochloride; Samarium/Lexidronam; Semustine; Simtrazene; Sparfosate Sodium; Sparsomycin; Spirogermanium Hydrochloride; Spiromustine; Spiroplatin; Squamocin; Squamotacin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trastuzumab; Trestolone Acetate; Triciribine Phosphate; Trimetrexate; Trimetrexate Glucuronate; Triptorelin; Tubulozole Hydrochloride; Uracil Mustard; Uredepa; Valrubicin; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid; 2-chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlorethamine); cyclophosphamide; melphalan; chlorambucil; ifosfamide; busulfan; N-methyl-N-nitrosourea (MNU); N, N'-Bis(2-chloroethyl)-N-nitrosourea (BCNU); N-(2-chloroethyl)-N'-cyclohexyl-N-nitrosourea (CCNU); N-(2-chloroethyl)-N'-(trans-4-methylcyclohexyl-N-nitrosourea (MeCCNU); N-(2-chloroethyl)-N'-(diethyl) ethylphosphonate-N-nitrosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis (platinum); tomudex; azacitidine; cytarabine; gemcitabine; 6-Mercaptopurine; 6-Thioguanine; Hypoxanthine; teniposide; 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); 2-chlorodeoxyadenosine (2-Cda).

Other chemotherapeutic compounds include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bleomycin $A_2$; bleomycin $B_2$; bropirimine; budotitane; buthionine sulfoximine; calcipotriol; calphostin C; camptothecin derivatives (e.g., 10-hydroxycamptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; 2' deoxycoformycin (DCF); deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones (A R=H; B R=Me); epithilones; epristeride; estramustine analogue; estrogen agonists; estrogen antagonists; etanidazole; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; hereguline; hexamethylene bisacetamide; homoharringtonine (HHT); hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mithracin; mitoguazone; mitolactol; mitomycin analogues; mitonafide; mitotoxin fibroblast growth factor-sap orin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin;

oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Other chemotherapies are those selected from the group consisting of: annonaceous acetogenins; asimicin; rolliniastatin; guanacone, squamocin, bullatacin; squamotacin; taxanes; paclitaxel; gemcitabine; methotrexate FR-900482; FK-973; FR-66979; FK-317; 5-FU; FUDR; FdUMP; Hydroxyurea; Docetaxel; discodermolide; epothilones; vincristine; vinblastine; vinorelbine; meta-pac; irinotecan; SN-38; 10-OH campto; topotecan; etoposide; adriamycin; flavopiridol; Cis-Pt; carbo-Pt; bleomycin; mitomycin C; mithramycin; capecitabine; cytarabine; 2-Cl-2'deoxyadenosine; Fludarabine-$PO_4$; mitoxantrone; mitozolomide; Pentostatin; Tomudex.

Other chemotherapeutics are taxanes (e.g., paclitaxel and docetaxel). Another important category of chemotherapeutic is annonaceous acetogenin.

Other chemotherapeutic are selected from the group consisting of aldesleukin, asparaginase, bleomycin sulfate, carboplatin, chlorambucil, cisplatin, cladribine, cyclophosphamide, cytarabine, dacarbazine, dactinomycin, daunorubicin hydrochloride, docetaxel, doxorubicin, doxorubicin hydrochloride, epirubicin hydrochloride, etoposide, etoposide phosphate, floxuridine, fludarabine, fluorouracil, gemcitabine, gemcitabine hydrochloride, hydroxyurea, idarubicin hydrochloride, ifosfamide, interferons, interferon-$\alpha$2a, interferon-$\alpha$2b, interferon-$\alpha$n3, interferon-$\alpha$1b, interleukins, irinotecan, mechlorethamine hydrochloride, melphalan, mercatopurine, methotrexate, methotrexate sodium, mitomycin, mitoxantrone, paclitaxel, pegaspargase, pentostatin, prednisone, profimer sodium, procabazine hydrochloride, taxol, taxotere, teniposide, topotecan hydrochloride, vinblastine sulfate, vincristine sulfate and vinorelbine tartrate.

Other chemotherapeutics include hormonal manipulation, particularly for breast and gynecological cancers, such as but not limited to tamoxifen or aromatase inhibitor arimidex (i.e., anastrozole).

Other chemotherapeutics include enzyme inhibitor agents such as CDK inhibitors, tyrosine kinase inhibitors, MAP kinase inhibitors, and EGFR inhibitors (e.g., C225).

Immune-Based Therapies

In some embodiments, RIC and/or RIC-like intervention is used to enhance immune-based therapies.

Immune-based therapies may be used to treat a variety of the conditions provided herein including but not limited to cancer. Immune-based therapies include vaccine therapies in which antigens are administered to a subject to induce an antigen-specific immune response. Immune-based therapies also include antibody therapies in which antibodies are administered to a subject to induce an antibody-based response such as antibody dependent cell-mediated cytoxicity (ADCC). A variety of immune-based therapies are known in the art. Non-limiting examples are provided below.

In some instances, the antibody therapy involves administering an antibody or antibody fragment selected from the group consisting of trastuzumab, alemtuzumab (B cell chronic lymphocytic leukemia), gemtuzumab ozogamicin (CD33+ acute myeloid leukemia), hP67.6 (CD33+ acute myeloid leukemia), infliximab (inflammatory bowel disease and rheumatoid arthritis), etanercept (rheumatoid arthritis), rituximab, tositumomab, MDX-210, oregovomab, anti-EGF receptor mAb, MDX-447, anti-tissue factor protein (TF), (Sunol); ior-c5, c5, edrecolomab, ibritumomab tiuxetan, anti-idiotypic mAb mimic of ganglioside GD3 epitope, anti-HLA-Dr10 mAb, anti-CD33 humanized mAb, anti-CD52 humAb, anti-CD1 mAb (ior t6), MDX-22, celogovab, anti-17-1A mAb, bevacizumab, daclizumab, anti-TAG-72 (MDX-220), anti-idiotypic mAb mimic of high molecular weight proteoglycan (I-Mel-1), anti-idiotypic mAb mimic of high molecular weight proteoglycan (I-Mel-2), anti-CEA Ab, hmAbH11, anti-DNA or DNA-associated proteins (histones) mAb, Gliomab-H mAb, GNI-250 mAb, anti-CD22, CMA 676), anti-idiotypic human mAb to GD2 ganglioside, ior egf/r3, anti-ior c2 glycoprotein mAb, ior c5, anti-FLK-2/FLT-3 mAb, anti-GD-2 bispecific mAb, antinuclear autoantibodies, anti-HLA-DR Ab, anti-CEA mAb, palivizumab, bevacizumab, alemtuzumab, BLyS-mAb, anti-VEGF2, anti-Trail receptor; B3 mAb, mAb BR96, breast cancer; and Abx-Cbl mAb.

In one important embodiment, the antibody or antibody fragment is an anti-HER2 antibody, and preferably it is trastuzumab. In another important embodiment, the antibody or antibody fragment is an anti-CD20 antibody, and preferably it is rituximab.

The antibody or antibody fragment may conjugated (covalently or otherwise) to a toxin derived from plant, fungus, or bacteria. The toxin may be selected from the group consisting of A chain toxin, deglycosylated A chain toxin, ribosome inactivating protein, α-sarcin, aspergillin, restrictocin, ribonuclease, diptheria toxin and *Pseudomonas* exotoxin, but is not so limited.

The antibody or antibody fragment may also conjugated to a chemotherapeutic agent, a radioisotope or a cytotoxin. The chemotherapeutic agent may be selected from the group consisting of an anti-metabolite, an anthracycline, a *vinca* alkaloid, an antibiotic, an alkylating agent, and an epipodophyllotoxin, but is not so limited. An example is an anti-HER2 antibody conjugated to a toxin.

The immune-based therapy may be a vaccine such as vaccine comprising a cancer antigen. Cancer antigens can be classified in a variety of ways. Cancer antigens include antigens encoded by genes that have undergone chromosomal alteration. Many of these antigens are found in lymphoma and leukemia. Even within this classification, antigens can be characterized as those that involve activation of quiescent genes. These include BCL-1 and IgH (Mantel cell lymphoma), BCL-2 and IgH (Follicular lymphoma), BCL-6 (Diffuse large B-cell lymphoma), TAL-1 and TCRalpha or SIL (T-cell acute lymphoblastic leukemia), c-MYC and IgH or IgL (Burkitt lymphoma), MUN/IRF4 and IgH (Myeloma), PAX-5 (BSAP) (Immunocytoma).

Other cancer antigens that involve chromosomal alteration and thereby create a novel fusion gene and/or protein include RAR-alpha, PML, PLZF, NPM or NuMA (Acute promyelocytic leukemia), BCR and ABL (Chronic myeloid/acute lymphoblastic leukemia), MLL (HRX) (Acute leukemia), E2A and PBX or HLF (B-cell acute lymphoblastic leukemia), NPM, ALK (Anaplastic large cell leukemia), and NPM, MLF-1 (Myelodysplastic syndrome/acute myeloid leukemia).

Other cancer antigens are specific to a tissue or cell lineage. These include cell surface proteins such as CD20, CD22 (Non-Hodgkin's lymphoma, B-cell lymphoma, Chronic lymphocytic leukemia (CLL)), CD52 (B-cell CLL), CD33 (Acute myelogenous leukemia (AML)), CD10 (gp100) (Common (pre-B) acute lymphocytic leukemia and malignant melanoma), CD3/T-cell receptor (TCR) (T-cell lymphoma and leukemia), CD79/B-cell receptor (BCR) (B-cell lymphoma and leukemia), CD26 (Epithelial and lymphoid malignancies) Human leukocyte antigen (HLA)-DR HLA-DP and HLA-DO (Lymphoid malignancies), RCAS1 (Gynecological carcinomas, bilary adenocarcinomas and ductal adenocarcinomas of the pancreas), and Prostate specific membrane antigen (Prostate cancer).

Tissue- or lineage-specific cancer antigens also include epidermal growth factor receptors (high expression) such as EGFR (HER1 or erbB1) and EGFRvIII (Brain, lung, breast, prostate and stomach cancer), erbB2 (HER2 or HER2/neu) (Breast cancer and gastric cancer), erbB3 (HER3) (Adenocarcinoma), and erbB4 (HER4) (Breast cancer).

Tissue- or lineage-specific cancer antigens also include cell-associated proteins such as Tyrosinase, Melan-A/MART-1, tyrosinase related protein (TRP)-1/gp75 (Malignant melanoma), Polymorphic epithelial mucin (PEM) (Breast tumors), and Human epithelial mucin (MUC1) (Breast, ovarian, colon and lung cancers).

Tissue- or lineage-specific cancer antigens also include secreted proteins such as Monoclonal immunoglobulin (Multiple myeloma and plasmacytoma), Immunoglobulin light chains (Multiple Myeloma), alpha-fetoprotein (Liver carcinoma), Kallikreins 6 and 10 (Ovarian cancer), Gastrin-releasing peptide/bombesin (Lung carcinoma), and Prostate specific antigen (Prostate cancer).

Still other cancer antigens are cancer testis (CT) antigens that are expressed in some normal tissues such as testis and in some cases placenta. Their expression is common in tumors of diverse lineages and as a group the antigens form targets for immunotherapy. Examples of tumor expression of CT antigens include MAGE-A1, -A3, -A6, -A12, BAGE, GAGE, HAGE, LAGE-1, NY-ESO-1, RAGE, SSX-1, -2, -3, -4, -5, -6, -7, -8, -9, HOM-TES-14/SCP-1, HOM-TES-85 and PRAME. Still other examples of CT antigens and the cancers in which they are expressed include SSX-2, and -4 (Neuroblastoma), SSX-2 (HOM-MEL-40), MAGE, GAGE, BAGE and PRAME (Malignant melanoma), HOM-TES-14/SCP-1 (Meningioma), SSX-4 (Oligodendrioglioma), HOM-TES-14/SCP-1, MAGE-3 and SSX-4 (Astrocytoma), SSX member (Head and neck cancer, ovarian cancer, lymphoid tumors, colorectal cancer and breast cancer), RAGE-1, -2, -4, GAGE-1, -2, -3, -4, -5, -6, -7 and -8 (Head and neck squamous cell carcinoma (HNSCC)), HOM-TES14/SCP-1, PRAME, SSX-1 and CT-7 (Non-Hodgkin's lymphoma), and PRAME (Acute lymphoblastic leukemia (ALL), acute myelogenous leukemia (AML) and chronic lymphocytic leukemia (CLL)).

Other cancer antigens are not specific to a particular tissue or cell lineage. These include members of the carcinoembryonic antigen (CEA) family: CD66a, CD66b, CD66c, CD66d and CD66e. These antigens can be expressed in many different malignant tumors and can be targeted by immunotherapy.

Still other cancer antigens are viral proteins and these include Human papilloma virus protein (cervical cancer), and EBV-encoded nuclear antigen (EBNA)-1 (lymphomas of the neck and oral cancer).

Still other cancer antigens are mutated or aberrantly expressed molecules such as but not limited to CDK4 and beta-catenin (melanoma).

The invention also embraces immune-based therapies that utilize antibodies that are specific for any of the foregoing cancer antigens.

Anti-Inflammatory Agents

Anti-inflammatory agents that may be used as a second therapy include but are not limited to Aspirin, ASA+Calcium Carbonate+Magnesium Oxide+Magnesium Carbonate, Aceclofenac, Balsalazide, Balsalazide Disodium, Betamethasone, Budesonide, Canakinumab, Choline Salicylate+Magnesium Salicylate, Cortisone, Dexamethasone, Diclofenac, Diclofenac Epolamine, Diclofenac+Misoprostol, Diclofenac Potassium, Diclofenac Sodium, Diflunisal, Drotrecogin Alfa, Etodolac, Fenoprofen, Hydrocortisone, Hydrocortisone Acetate, Loteprednol, Lumiracoxib, Nimesulide, Naproxen), Magnesium Salicylate, Magnesium Salicylate+Phenyltoloxamine, Meclofenamate, Mefenamic Acid, Mesalamine, Mesalamine, 5-ASA, Methylprednisolone, Misoprostol, Olsalazine, Oxaprozin, Oxaprozin Potassium, Prednisone, Rilonacept, Rimexolone, Sulfasalazine, Sulindac, Tolmetin, Triamcinolone Acetonide, and Valdecoxib.

Additional anti-inflammatory agents that may be used as a second therapy include but are not limited to A-hydroCort (Hydrocortisone), A-methaPred (Methylprednisolone), Aceclofenac, Ainex (Nimesulide), Aldoron (Nimesulide), Aleve (Naproxen), Algolider (Nimesulide), Anaprox (Naproxen), Antiflogil (Nimesulide), Antifloxil (Nimesulide), Anucort-HC (Hydrocortisone), Anusol-HC (Hydrocortisone), Apriso (Mesalamine), Arcalyst (Rilonacept), Arthrotec (Diclofenac+Misoprostol), Asacol (Mesalamine 5-ASA) Aspirin (ASA+Calcium Carbonate+Magnesium Oxide+Magnesium Carbonate), Aulin (Nimesulide), Azulfidine (Sulfasalazine), Balsalazide, Beta-Val (Betamethasone), Betamethasone, Betatrex (Betamethasone), Bextra (Valdecoxib), Budesonide, Bufferin (Aspirin, ASA+Calcium Carbonate+Magnesium Oxide+Magnesium) Carbonate, Cambia (Diclofenac), Canakinumab, Canasa (Mesalamine, 5-ASA), Cataflam (Diclofenac), Celestamine F (Betamethasone), Celestone (Betamethasone), Celestone IM (Betamethasone), Choline Salicylate+Magnesium Salicylate, Clinoril (Sulindac), CMT (Choline Salicylate+Magnesium Salicylate), Colazal (Balsalazide), Colocort (Hydrocortisone), Cortaid (Hydrocortisone), Cortef (Hydrocortisone), Cortenema (Hydrocortisone), Cortifoam (Hydrocortisone), Cortizone-10 (Hydrocortisone), Cortizone-5 (Hydrocortisone), Cortone (Cortisone), Cortone IM (Cortisone), Cytotec (Misoprostol), Daypro (Oxaprozin), Daypro Alta (Oxaprozin Potassium), Decadron (Dexamethasone), Decadron IM/IV (Dexamethasone), Decadron-LA (Dexamethasone), Decaspray (Dexamethasone), Deflogen (Nimesulide), Deltasone (Prednisone), Delzicol (Mesalamine), Dexamethasone, Dexpak Dexamethasone, Diclofenac, Diclofenac+Misoprostol, Diflunisal, Dipentum (Olsalazine), Diprolene (Betamethasone), Diprosone (Betamethasone), Doan's (Magnesium Salicylate), Dolobid (Diflunisal), Donulide (Nimesulide), Drotrecogin Alfa, Entocort EC (Budesonide), Eskaflam (Nimesulide), Etodolac, Eudolene (Nimesulide), Fansidol (Nimesulide), Fenoprofen, Flector (Diclofenac Epolamine), Flogovital N.F (Nimesulide), Flolid (Nimesulide), Giazo (Balsalazide Disodium), Guaxan (Nimesulide), Hemril-HC (Hydrocortisone), Heugan (Nimesulide), Hexadrol (Dexamethasone), Hydrocortisone, Hydrocortone (Hydrocortisone), Hydrocortone Acetate (Hydrocortisone), Hytone (Hydrocortisone), Ilaris (Canakinumab), Jabasulide (Nimesulide), Laidor (Nimesulide), Ledoren (Nimesulide), Lialda (Mesalamine), Locoid (Hydrocortisone), Lodine (Etodolac), Lodine XL (Etodolac), Lotemax (Loteprednol), Loteprednol, Lumiracoxib, Luxiq Foam (Betamethasone), Magnesium Salicylate, Magnesium Salicylate+Phenyltoloxamine, Magsal (Magnesium Salicylate+Phenyltoloxamine), Maxivate (Betamethasone), Meclofenamate, Mefenamic Acid, Medrol (Methylprednisolone), Medrol DosePak (Methylprednisolone), Mesalamine, Mesid (Nimesulide), Mesulid (Nimesulide), Metaflex (Nimesulide), MF/110 (Nimesulide), Micort-hc (Hydrocortisone Acetate), Misoprostol, Mobidin (Magnesium Salicylate) Mobigesic (Magnesium Salicylate+Phenyltoloxamine) Momentum (Magnesium Salicylate), Nalfon (Fenoprofen), Naprelan (Naproxen), Napron X (Naproxen), Naprosyn (Naproxen), Naproxen, Nexen (Nimesulide), Nide (Nimesulide), Nidol (Nimesulide), Nimed (Nimesulide), Nimedex (Nimesulide), Nimesil (Nimesulide), Nimesulene (Nimesulide), Nimesulide, Nimesulide Dorom (Nimesulide), Nimind (Nimesulide), Nims (Nimesulide), Nimulid (Nimesulide), Nisal (Nimesulide), Nisulid (Nimesulide), Octaprin (Nimesulide), Olsalazine, Orasone (Prednisone), Oxaprozin, Ozurdex (Dexamethasone), Pandel (Hydrocortisone), Pennsaid (Diclofenac Sodium), Pentasa (Mesalamine, 5-ASA), Ponstel (Meclofenamate, Mefenamic Acid), Prednisone, Prexige (Lumiracoxib), Proctocort (Hydrocortisone), Pulmicort (Budesonide), Rayos (Prednisone), Remov (Nimesulide), Resulin (Nimesulide), Rhinocort (Budesonide), Rhinocort Aqua (Budesonide), Rilonacept, Rimexolone, Rowasa (Mesalamine, 5-ASA), Salofalk (Mesalamine, 5-ASA), Scaflam (Nimesulide), Scaflan (Nimesulide), Scalid (Nimesulide), Sintalgin (Nimesulide), Solaraze (Diclofenac), Solu-Cortef (Hydrocortisone), Solu-Medrol (Methylprednisolone), Sulfasalazine, Sulide (Nimesulide), Sulidene (Nimesulide), Sulimed (Nimesulide), Sulindac, Teonim (Nimesulide), Tolectin (Tolmetin), Tolmetin, Tricosal (Choline Salicylate+Magnesium Salicylate), Triesence (Triamcinolone Acetonide), Trilisate (Choline Salicylate+Magnesium Salicylate), Trisalcid (Choline Salicylate+Magnesium Salicylate), Trivaris (Triamcinolone Acetonide), Uceris (Budesonide), Uticort (Betamethasone), Valdecoxib, Valisone (Betamethasone), Vexol (Rimexolone), Voltaren (Diclofenac), Westcort (Hydrocortisone), Xigris (Drotrecogin Alfa), and Zipsor (Diclofenac Potassium).

Expression Level Analysis

The invention therefore contemplates methods that involve measuring the mRNA or protein levels for autophagy markers and comparing such levels to control levels, including for example predetermined thresholds.

mRNA Assays

The art is familiar with various methods for analyzing mRNA levels. Examples of mRNA-based assays include but are not limited to oligonucleotide microarray assays, quantitative RT-PCR, Northern analysis, and multiplex bead-based assays.

Expression profiles of cells in a biological sample (e.g., blood or a tumor) can be carried out using an oligonucleotide microarray analysis. As an example, this analysis may be carried out using a commercially available oligonucleotide microarray or a custom designed oligonucleotide microarray comprising oligonucleotides for all or a subset of the transcripts described herein. The microarray may comprise any number of the transcripts, as the invention contemplates that elevated risk may be determined based on the analysis of single differentially expressed transcripts or a combination of differentially expressed transcripts. The transcripts may be those that are up-regulated in tumors carrying a germ-line risk marker (compared to a tumor that does not carry the germ-line risk marker), or those that are down-regulated in tumors carrying a germ-line risk marker (compared to a tumor that does not carry the germ-line risk marker), or a combination of these. The number of transcripts measured using the microarray therefore may be 1, 2, 3, 4, 5, 6, 7, 8, 9, or more transcripts encoded by a gene in Table 2 or 3. It is to be understood that such arrays may however also comprise positive and/or negative control transcripts such as housekeeping genes that can be used to determine if the array has been degraded and/or if the sample has been degraded or contaminated. The art is familiar with the construction of oligonucleotide arrays.

Commercially available gene expression systems include Affymetrix GeneChip microarrays as well as all of Illumina standard expression arrays, including two GeneChip 450 Fluidics Stations and a GeneChip 3000 Scanner, Affymetrix High-Throughput Array (HTA) System composed of a GeneStation liquid handling robot and a GeneChip HT Scanner providing automated sample preparation, hybridization, and scanning for 96-well Affymetrix PEGarrays. These systems can be used in the cases of small or potentially degraded RNA samples. The invention also contemplates analyzing expression levels from fixed samples (as compared to freshly isolated samples). The fixed samples include formalin-fixed and/or paraffin-embedded samples. Such samples may be analyzed using the whole genome Illumina DASL assay. High-throughput gene expression profile analysis can also be achieved using bead-based solutions, such as Luminex systems.

Other mRNA detection and quantitation methods include multiplex detection assays known in the art, e.g., xMAP® bead capture and detection (Luminex Corp., Austin Tex.)

Another exemplary method is a quantitative RT-PCR assay which may be carried out as follows: mRNA is extracted from cells in a biological sample (e.g., blood or a tumor) using the RNeasy kit (Qiagen). Total mRNA is used for subsequent reverse transcription using the SuperScript III First-Strand Synthesis SuperMix (Invitrogen) or the SuperScript VILO cDNA synthesis kit (Invitrogen). 5 µl of the RT reaction is used for quantitative PCR using SYBR Green PCR Master Mix and gene-specific primers, in triplicate, using an ABI 7300 Real Time PCR System.

mRNA detection binding partners include oligonucleotide or modified oligonucleotide (e.g. locked nucleic acid) probes that hybridize to a target mRNA. Probes may be designed using the sequences or sequence identifiers listed in Table 2 or 3. Methods for designing and producing oligonucleotide probes are well known in the art (see, e.g., U.S. Pat. No. 8,036,835; Rimour et al. GoArrays: highly dynamic and efficient microarray probe design. Bioinformatics (2005) 21 (7): 1094-1103; and Wernersson et al. Probe selection for DNA microarrays using OligoWiz. Nat Protoc. 2007; 2(11): 2677-91).

Protein Assays

The art is familiar with various methods for measuring protein levels. Protein levels may be measured using protein-based assays such as but not limited to immunoassays, Western blots, Western immunoblotting, multiplex bead-based assays, and assays involving aptamers (such as SOMAmer™ technology) and related affinity agents.

A brief description of an exemplary immunoassay is provided here. A biological sample is applied to a substrate having bound to its surface protein-specific binding partners (i.e., immobilized protein-specific binding partners). The protein-specific binding partner (which may be referred to as a "capture ligand" because it functions to capture and immobilize the protein on the substrate) may be an antibody or an antigen-binding antibody fragment such as Fab, F(ab)2, Fv, single chain antibody, Fab and sFab fragment, F(ab')2, Fd fragments, scFv, and dAb fragments, although it is not so limited. Other binding partners are described herein. Protein present in the biological sample bind to the capture ligands, and the substrate is washed to remove unbound material. The substrate is then exposed to soluble protein-specific binding partners (which may be identical to the binding partners used to immobilize the protein). The soluble protein-specific binding partners are allowed to bind to their respective proteins immobilized on the substrate, and then unbound material is washed away. The substrate is then exposed to a detectable binding partner of the soluble protein-specific binding partner. In one embodiment, the soluble protein-specific binding partner is an antibody having some or all of its Fc domain. Its detectable binding partner may be an anti-Fc domain antibody. As will be appreciated by those in the art, if more than one protein is being detected, the assay may be configured so that the soluble protein-specific binding partners are all antibodies of the same isotype. In this way, a single detectable binding partner, such as an antibody specific for the common isotype, may be used to bind to all of the soluble protein-specific binding partners bound to the substrate.

It is to be understood that the substrate may comprise capture ligands for one or more proteins, including two or more, three or more, four or more, five or more, etc. up to and including all of the proteins encoded by the genes in Table 2 provided by the invention.

Other examples of protein detection and quantitation methods include multiplexed immunoassays as described for example in U.S. Pat. Nos. 6,939,720 and 8,148,171, and published US Patent Application No. 2008/0255766, and protein microarrays as described for example in published US Patent Application No. 2009/0088329.

Protein detection binding partners include protein-specific binding partners. Protein-specific binding partners can be generated using the sequences or sequence identifiers listed in Table 2. In some embodiments, binding partners may be antibodies. As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')2, Fd fragments, Fv fragments, scFv, and dAb fragments) as well as complete antibodies. Methods for making antibodies and antigen-binding fragments are well known in the art (see e.g., Sambrook et al, "Molecular Cloning: A Laboratory Manual" (2nd Ed.), Cold Spring Harbor Laboratory Press (1989); Lewin, "Genes IV", Oxford University Press, New York, (1990), and Roitt et al., "Immunology" (2nd Ed.), Gower Medical Publishing, London, New York (1989), WO2006/040153, WO2006/122786, and WO2003/002609).

Binding partners also include non-antibody proteins or peptides that bind to or interact with a target protein, e.g., through non-covalent bonding. For example, if the protein is a ligand, a binding partner may be a receptor for that ligand. In another example, if the protein is a receptor, a binding partner may be a ligand for that receptor. In yet another example, a binding partner may be a protein or peptide known to interact with a protein. Methods for producing proteins are well known in the art (see, e.g. Sambrook et al, "Molecular Cloning: A Laboratory Manual" (2nd Ed.), Cold Spring Harbor Laboratory Press (1989) and Lewin, "Genes IV", Oxford University Press, New York, (1990)) and can be used to produce binding partners such as ligands or receptors.

Binding partners also include aptamers and other related affinity agents. Aptamers include oligonucleic acid or peptide molecules that bind to a specific target. Methods for producing aptamers to a target are known in the art (see, e.g., published US Patent Application No. 2009/0075834, U.S. Pat. Nos. 7,435,542, 7,807,351, and 7,239,742). Other examples of affinity agents include SOMAmer™ (Slow Off-rate Modified Aptamer, SomaLogic, Boulder, Colo.) modified nucleic acid-based protein binding reagents.

Binding partners also include any molecule capable of demonstrating selective binding to any one of the target proteins disclosed herein, e.g., peptoids (see, e.g., Reyna J Simon et al., "Peptoids: a modular approach to drug discovery" Proceedings of the National Academy of Sciences USA, (1992), 89(20), 9367-9371; U.S. Pat. No. 5,811,387; and M. Muralidhar Reddy et al., Identification of candidate IgG biomarkers for Alzheimer's disease via combinatorial library screening. Cell 144, 132-142, Jan. 7, 2011).

Detectable Labels

Detectable binding partners may be directly or indirectly detectable. A directly detectable binding partner may be labeled with a detectable label such as a fluorophore. An indirectly detectable binding partner may be labeled with a moiety that acts upon (e.g., an enzyme or a catalytic domain) or a moiety that is acted upon (e.g., a substrate) by another moiety in order to generate a detectable signal. Exemplary detectable labels include, e.g., enzymes, radioisotopes, haptens, biotin, and fluorescent, luminescent and chromogenic substances. These various methods and moieties for detectable labeling are known in the art.

Controls

Some of the methods provided herein involve measuring a level and then comparing that level to a control in order to measure autophagy levels. The control may be a control level that is a level in a control tissue, control subject, or a population of control subjects.

The control may be (or may be derived from) a normal subject (or normal subjects). A normal subject, as used herein, refers to a subject that is healthy. The control population may be a population of normal subjects.

It is to be understood that the methods provided herein do not require that a control level be measured every time a subject is tested. Rather, it is contemplated that control levels are obtained and recorded and that any test level is compared to such a predetermined level (or threshold).

EXAMPLES

Experimental Procedures

Animals and subjects: All animal protocols were approved by the Animal Care and Use Committee of the Hospital for Sick Children in Toronto and conformed to the Guide for the Care and Use of Laboratory Animals published by the National Institutes of Health (NIH publication No. 85-23, revised 1996).

Induction of Remote Ischemic Conditioning (rIC or rIPC):

C57BL/6 male mice (8-10 weeks) were anesthetized with pentobarbital (60 mg/kg intraperitoneally). Remote IC was induced by four cycles of 5 minutes of limb ischemia (by tourniquet) followed by 5 minutes reperfusion as previously described (Kharbanda et al. Circulation 2001, 103:1624; Konstantinov et al. J Thorac Cardiovasc Surg 2005 130:1326) Animals were divided into 3 groups (first window: a single RIC episode with sacrifice within 1 hour; second window: a single RIC episode with sacrifice 24 hours later; and a third window that underwent daily RIC for 10 days with sacrifice 24 hours after the last episode). The $3^{rd}$ window group and the 10 day RIC group are the same.

Immunoblotting:

Western blotting was conducted according to standard protocols. Anti-phosphorylated-Akt (p-Akt) (62 kDa, Thr172), anti-mTOR (289 kDa, Ser2481), anti-Beclin-1 (60 kDa), anti-LC3II/I (19 kDa for I, 17 kDa for II), anti-p62 (60 kDa), anti-capthesin-L (23 kDa), and anti-Atg5 antibodies were used as primary antibodies. Immunoblots were scanned using an Odyssey LI-COR and quantified using Image Studio.

Mouse Langendorff Preparation and Global Ischemia/Reperfusion Model:

In order to examine the myocardial effects of the interventions, without the potential confounding effects on other systems, isolated mouse hearts were mounted on the Langendorff perfusion apparatus as previously described (Kharbanda et al. Circulation 2001, 103:1624; Konstantinov et al. J Thorac Cardiovasc Surg 2005, 130:1326) and perfused under non-recirculating conditions at a constant pressure of 80 mmHg with 37° C. Krebs-Henseleit buffer (KHB). Then a balloon, made with saran wrap and PE60 polyethylene tubing, was inserted into left ventricular (LV) through the mitral valve and was connected to a pressure transducer. The balloon was inflated with water to adjust left ventricular end-diastolic pressure (LVEDP) to 7-10 mmHg at the beginning of the experiment and the volume kept constant for the duration of the study. After a 20 min stabilization period, hearts were subjected to 30 min of no-flow global ischemia followed by 60 min of reperfusion. Hemodynamic measurements, including heart rate (HR), peak left ventricular pressure (LVP), maximum rate of contraction (+dP/dtmax), maximum rate of relaxation (−dP/dtmin), and LVEDP are recorded on a data acquisition system (PowerLab, ADInstruments) throughout the procedure.

Measurement of Infarct Size:

Infarct size was assessed via 1.25% 2,3,5-triphenyltetrazolium chloride (TTC, Sigma) staining as described previously (Kharbanda et al. Circulation 2001, 103:1624; Konstantinov et al. J Thorac Cardiovasc Surg 2005, 130:1326).

Example 1

Mice were randomized to control (HC, first bar of each pairing) or chronic remote ischemic conditioning (RIC, second bar of each pairing) daily to the leg for 10 days. Western blotting of heart specimens was then performed to assess level of autophagy signaling such as increased LC3II and capthesin L protein responses. FIG. 1 indicates increases in a variety of autophagy signaling pathways following RIC.

Example 2

Figure 2:
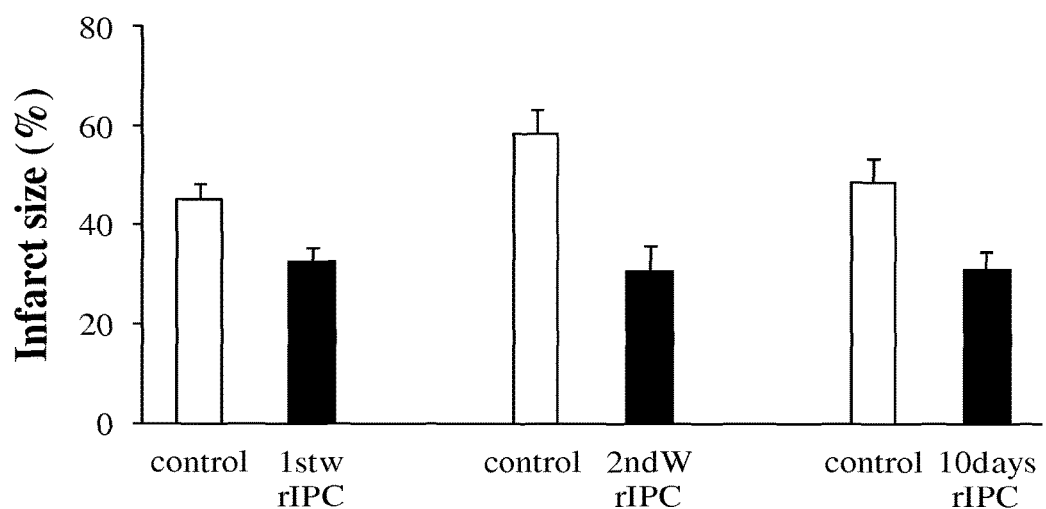
FIG. 2. Infarct size as a function of $1^{st}$, $2^{nd}$, and $3^{rd}$ window (10 days) of rIPC relative (left to right) to untreated controls (first bar of each bar pairing). Treated mice are the second bar of each bar pairing.

Mice were randomized to control or rIPC groups. The rIPC groups are denoted $1^{st}$ window rIPC or RIC, $2^{nd}$ window rIPC or RIC, $3^{rd}$ window rIPC or RIC (same as 10 day rIPC or RIC). Each group was subjected to ischemic-reperfusion injury as described for example by Kharbanda et al. Circulation 2001, 103:1624; Konstantinov et al. J Thorac Cardiovasc Surg 2005, 130:1326. Data are presented as infarct size relative to a normalized control. The infarct size was decreased relative to untreated control in each of the rIPC groups (FIG. 2).

Autophagy protein marker expression was also analyzed at 1 hour ($1^{st}$ window RIC) and 24 hours ($2^{nd}$ window RIC) after a single RIC event, and 24 hours after the last of 10 daily RIC events ($3^{rd}$ window or 10 day RIC) (without ischemic-reperfusion injury). P-AMPKa was expressed at a higher level (relative to control) within one hour after a single RIC but at a lower level (relative to control) at 24 hours after a single RIC, and at 24 hours after 10 daily RIC events (FIGS. 3-5).

Figure 3:
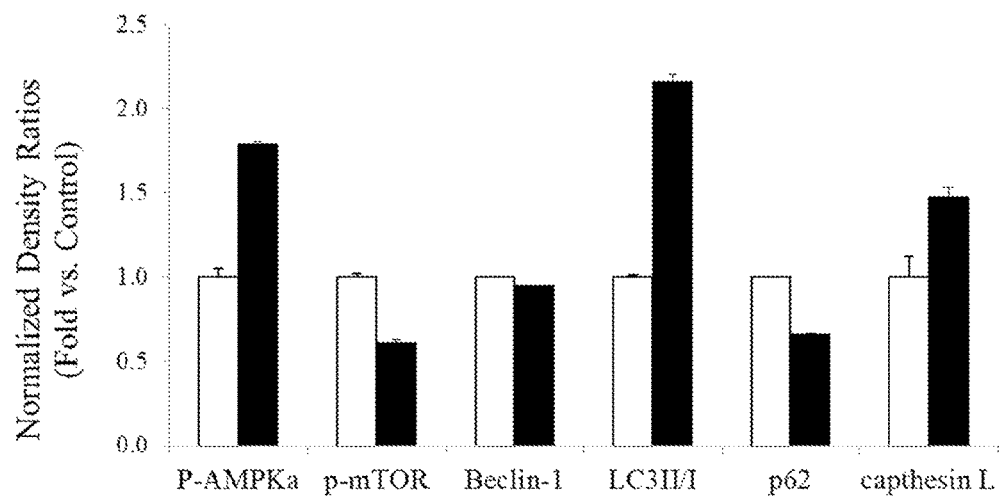
FIG. 3. Expression of autophagy protein markers measured in myocardium of mice after a $1^{st}$ window rIPC. The first bar of each pairing represents a sham control and the second bar represents the rIPC treated mouse. For FIGS. 3-5, markers from left to right are p-AMPKa, p-mTOR, Beclin-1, LC3 II/I, p62 and capthesin L.
Figure 4:
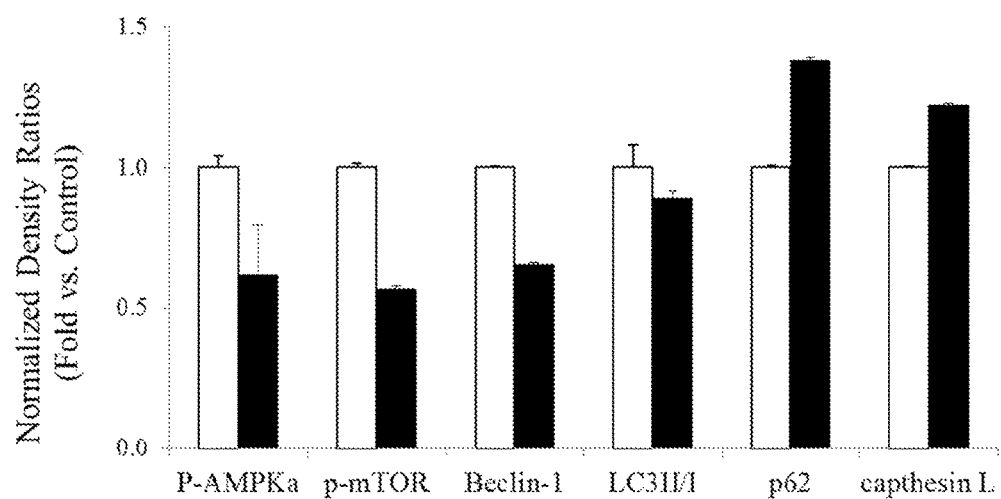
FIG. 4. Expression of autophagy protein markers measured in myocardium of mice after a $2^{nd}$ window rIPC. The first bar of each pairing represents a sham control and the second bar represents the rIPC treated mouse.
Figure 5:
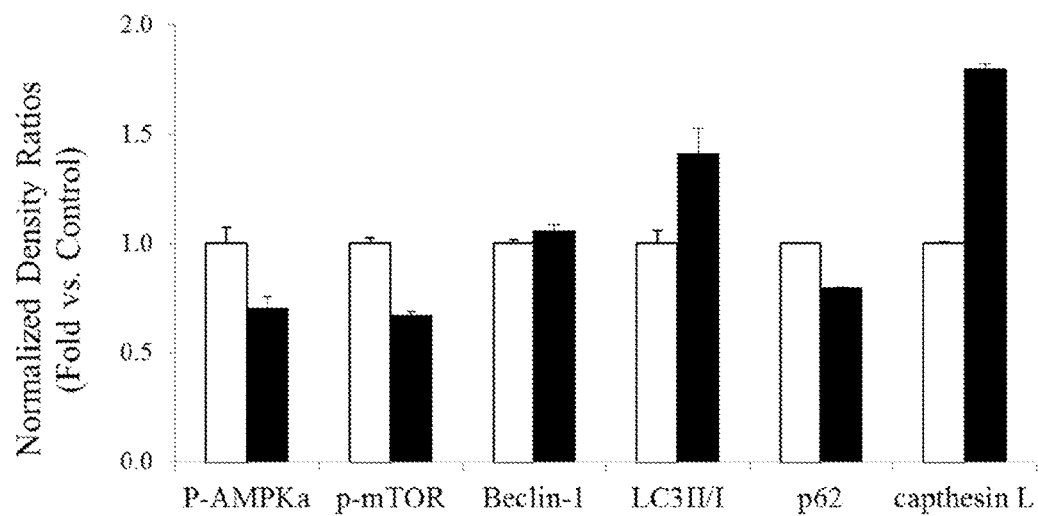
FIG. 5. Expression of autophagy protein markers measured in myocardium of mice after a $3^{rd}$ window rIPC. The first bar of each pairing represents a sham control and the second bar represents the rIPC treated mouse.

Other autophagy protein markers remained up-regulated (e.g., capthesin L) or down-regulated (e.g., p-mTOR) in all the RIC groups (FIGS. 3-5).

Figure 6:
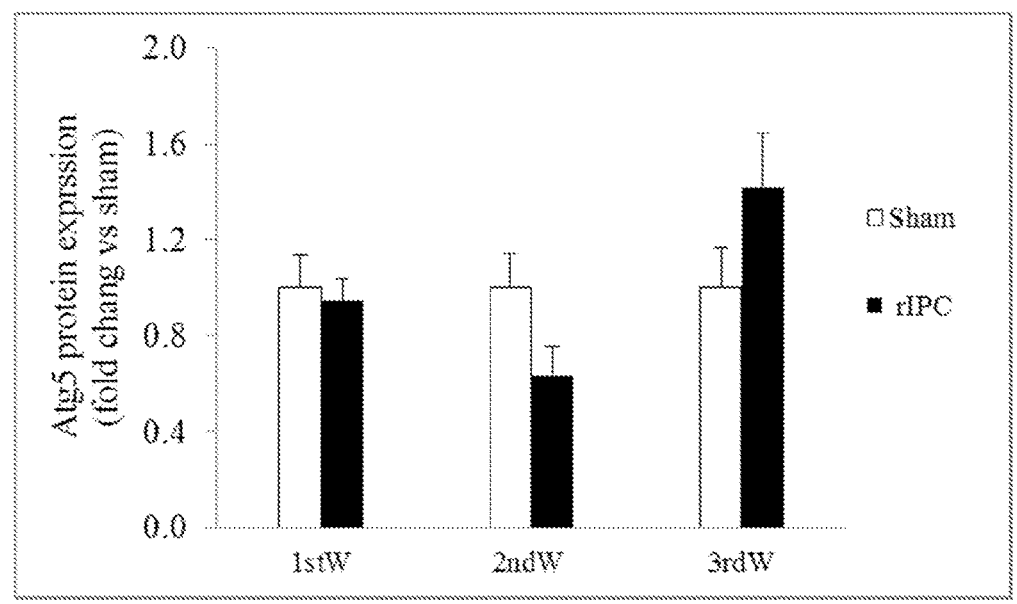
FIG. 6. Expression of Atg5 protein in myocardium of mice (fold change vs. sham) after a $1^{st}$ window, a $2^{nd}$ window and a $3^{rd}$ window of rIPC (from left to right). The first bar of each pairing represents the sham control and the second bar represents the rIPC treated mouse.

Atg5 protein expression is down-regulated (relative to control) at 1 and 24 hours after a single RIC event. At 24 hours after 10 daily RIC events, Atg5 is up-regulated (relative to control) (FIG. 6).

Other Embodiments

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Each reference referred to herein is incorporated by reference herein in its entirety.

What is claimed is:

1. A method comprising
performing remote ischemic conditioning (RIC) on a limb of a subject having a condition that benefits from enhanced autophagy,
wherein RIC comprises two or more cycles of blood flow occlusion followed by reperfusion, wherein each cycle has a blood flow occlusion duration of one minute or more and wherein a second or subsequent cycle begins upon conclusion of reperfusion of a previous cycle, and
wherein the condition is Alzheimer's disease, Parkinson's disease or Huntington's disease.

2. The method of claim 1, wherein the RIC is chronic RIC.

3. The method of claim 1, wherein the RIC is acute RIC.

4. The method of claim 1, wherein RIC is performed on a daily basis.

5. The method of claim 1, wherein RIC is performed more than once a day.

6. The method of claim 1, wherein RIC is performed on at least a daily basis for at least one month, two months, three months, four months, five months, six months, seven months, eight months, nine months, ten months, eleven months, or a year.

7. The method of claim 1, wherein RIC is performed every other day for at least one month, two months, three months, four months, five months, six months, seven months, eight months, nine months, ten months, eleven months, or a year.

8. The method of claim 1, wherein RIC comprises 3, 4, 5 or more cycles, each cycle comprising a blood occlusion period and a reperfusion period.

9. The method of claim 1, wherein each cycle comprising a 5 minute blood occlusion period and a 5 minute reperfusion period.

10. The method of claim 1, wherein the subject is receiving another therapy.

11. The method of claim 10, wherein the other therapy is administered at less than a maximum tolerable dose.

12. The method of claim 10, wherein the other therapy is administered at greater than the maximum tolerable dose.

13. The method of claim 1, wherein the condition is Alzheimer's disease.

14. The method of claim 1, wherein the condition is Huntington's disease.

15. The method of claim 1, wherein the condition is Parkinson's disease.

16. The method of claim 1, wherein RIC is performed using a device comprising
 a cuff configured to retract around the limb of the subject,
 an actuator connected to the cuff that causes the cuff to contract about the limb to reduce blood flow there through, and
 a controller that controls the actuator.

17. The method of claim 1, wherein the condition is not associated with ischemia/reperfusion injury.

* * * * *